Figure 1:
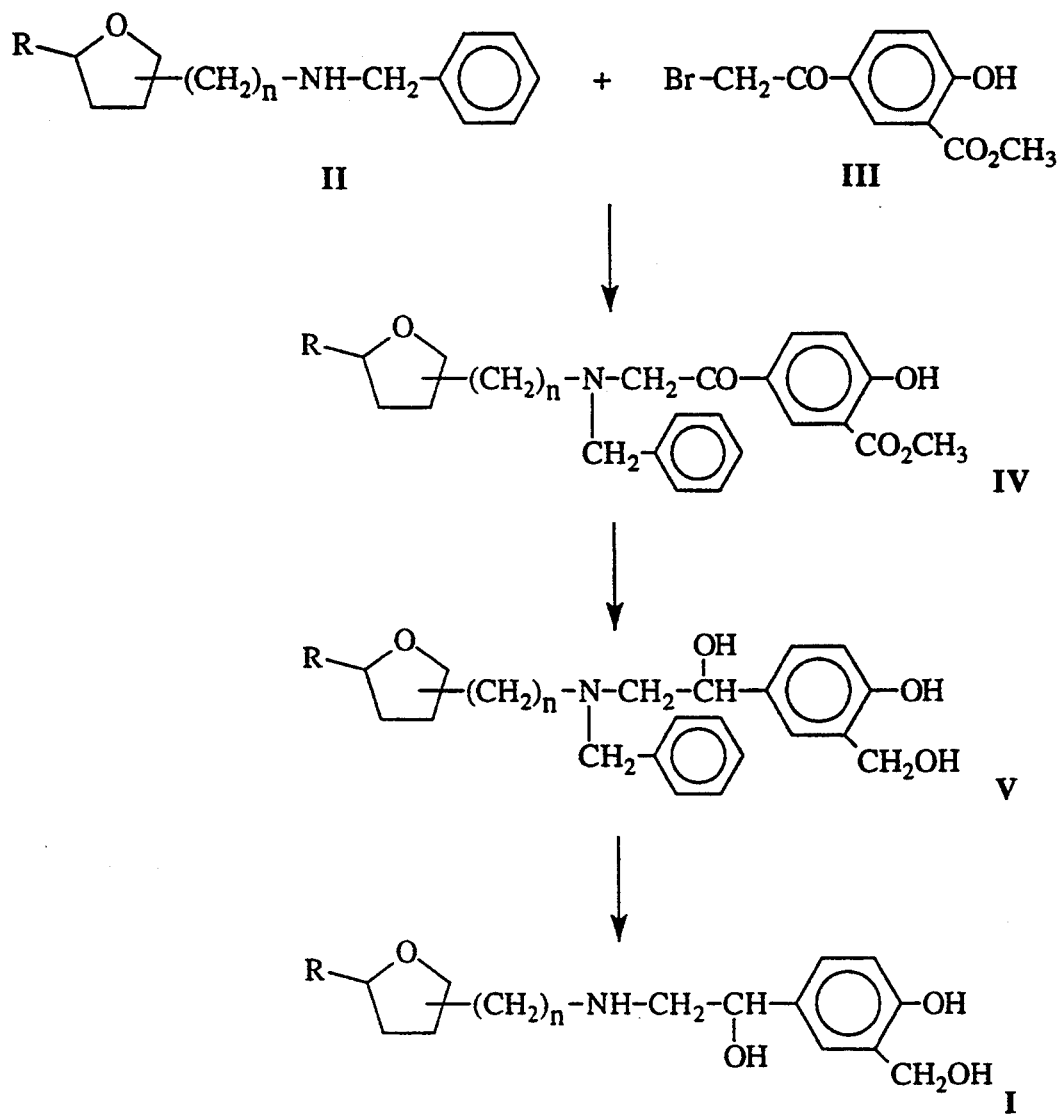

United States Patent [19]

Auvin et al.

[11] Patent Number: 5,447,942
[45] Date of Patent: Sep. 5, 1995

[54] N-DERIVATIVES OF (PHENYLETHYL-β-OL) AMINE, A PROCESS FOR THEIR PREPARATION AND PHARAMACEUTICAL COMPOSITIONS CONTAINING THE SAME

[75] Inventors: Serge Auvin, St Michel; Pierre Braquet, Garches; Colette Broquet, Boulogne, all of France

[73] Assignee: Societe de Conseils de Recherches et d'Applications Scientifiques (S.C.R.A.S.), France

[21] Appl. No.: 91,589

[22] Filed: Jul. 13, 1993

[30] Foreign Application Priority Data

Jul. 17, 1992 [GB] United Kingdom ............. 9215274

[51] Int. Cl.$^6$ ............ A61K 31/44; A61K 31/34; C07D 307/12; C07D 307/14
[52] U.S. Cl. ................. 514/336; 514/471; 514/473; 546/283; 549/495
[58] Field of Search ............ 549/495; 546/283; 54/336, 471, 473

[56] References Cited

FOREIGN PATENT DOCUMENTS 422889  4/1991 European Pat. Off. .
2140800 12/1984 United Kingdom .
2230525 10/1990 United Kingdom .
2230775 10/1990 United Kingdom .

OTHER PUBLICATIONS

Thompson, A. S. et al., "Conversion of a Silylated Hemiacetal into an a–Bromoether Using Trimethylsilyl-bromide", Tetrahedron Letters, vol. 31, No. 48, pp. 6953–6956 (1990).

Konzett and Rossler, "Versuchsanordunung zu Untersuchungen an der Bronchialmuskulatur", Pharmakologischen Institute der Universitate Wien, 1940.

Chandrasekharan, J. et al., "Diisopinocampheyl-chloroborane, a Remarkably Efficient Chiral Reducing Agent for Aromatic Prochiral Ketones", J. Org. Chem., 1985, 50, 5446–5448.

Collin et al., "Saligenin Analogs of Sympathomimetic Catecholamines", Journal of Medicinal Chemstry, vol. 13, No. 4, 1970, pp. 674–680.

*Primary Examiner*—C. Warren Ivy
*Assistant Examiner*—Ba K. Trinh
*Attorney, Agent, or Firm*—Lucas & Just

[57] ABSTRACT

The invention relates to a N-(2,4- or 2,5-disubstituted tetrahydrofuryl alkyl)-N-(phenylethyl-β-ol)amine derivative, under a racemic or enantiomer form, of general formula I

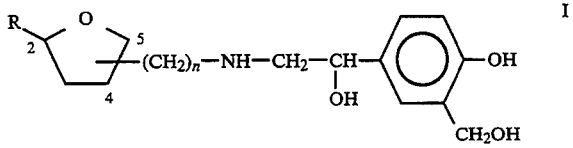

wherein R represent various radicals and n is of from 1 to 10, to a process for the preparation of said derivative, and to pharmaceutical compositions comprising the same.

6 Claims, 6 Drawing Sheets

Reaction scheme 1

Reaction scheme 2

Reaction scheme 6

N-DERIVATIVES OF (PHENYLETHYL-$\beta$-OL) AMINE, A PROCESS FOR THEIR PREPARATION AND PHARAMACEUTICAL COMPOSITIONS CONTAINING THE SAME The invention relates to N-derivatives of (phenylethyl-$\beta$-ol)amine, their processes of preparation, and pharmaceutical compositions based thereon. These products are agonists of $\beta$-adrenergic receptors.

The invention provides a N-(2,4- or 2,5-disubstituted tetrahydrofuryl alkyl)-N-(phenylethyl-$\beta$-ol)amine derivative, under a racemic or enantiomer form, of general formula I

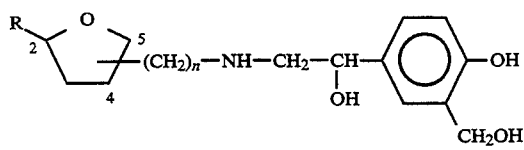

wherein
R represents a straight or branched alkyl group comprising from 1 to 10 carbon atoms; an heteroaryl group, a phenyl radical or a substituted phenyl radical of the formula

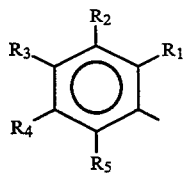

in which the radicals $R_1$, $R_2$, $R_3$, $R_4$ and $R_5$ independently represent a hydrogen atom, a halogen atom, an alkoxy radical comprising from 1 to 5 carbon atoms, or an alkylsulphonyl radical comprising from 1 to 5 carbon atoms;
n is from 1 to 10;
and pharmaceutically acceptable salts thereof. Such salts are formed from organic or mineral acids, such as hydrochloric, hydrobromic, sulphuric, fumaric or maleic acid.

The state of the art may be illustrated by British patent application No. 2 230 775, British patent application No. 2 140 800 and European patent application No. 422 889: said patent applications refer to ether-like compounds, with an ether bond instead of the —(CH$_2$)$_n$— chain of the compounds of the invention.

The invention also provides a process for the preparation of a compound of formula I, the said process comprising the following steps:
condensation of a substituted benzylamine of general formula II

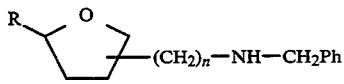

with methyl 5-bromoacetyl salicylate III, in a protic solvent or acetonitrile, in presence of triethylamine, at a temperature of from room temperature to the boiling point of the reaction mixture, for 2 to 18 hours, then reduction, under inert atmosphere, with an hydride as reducing agent, in an ethereal solvent, for 2 to 8 hours, at a temperature of from 0° C. to room temperature, of compound IV so obtained of the formula

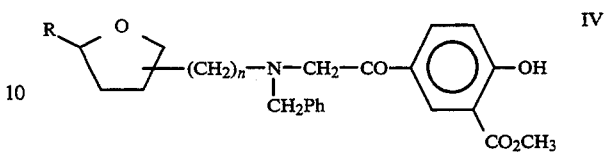

and finally, debenzylation of compound V of the formula

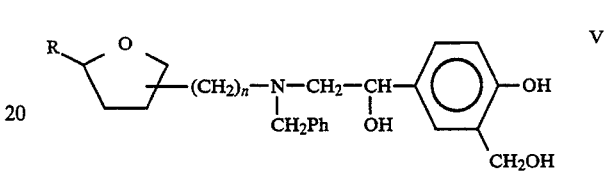

by hydrogenation in presence of an appropriate catalyst, at 2 to 5.5 bar, at a temperature of from room temperature to 40° C. for 10 minutes to 5 hours.

According to the invention, the condensation reaction may be performed in a protic solvent such as, for instance, dimethyl sulfoxide. In the reduction reaction, the reducing agent used may be preferably hydrides such as, for instance, LiAlH$_4$; the reaction may be carried out in an ethereal solvent such as, for instance, tetrahydrofuran or diethyl ether. In the debenzylation reaction, the appropriate catalyst may be selected of from Pd/C or PtO$_2$. In a preferred embodiment, when R stands for a heteroaryl group or a phenyl radical substituted by one or more halogen atoms, the debenzylation may be performed with PtO$_2$ as catalyst, at room temperature, for 10 to 30 minutes and at 4-5.5 bar. In an other preferred embodiment, when R stands for an alkyl group or a phenyl radical optionally substituted by one or more alkoxy or alkylsulphonyl radicals, the debenzylation may be performed with Pd/C (10%) at 2-3.5 bar.

Figure 2:
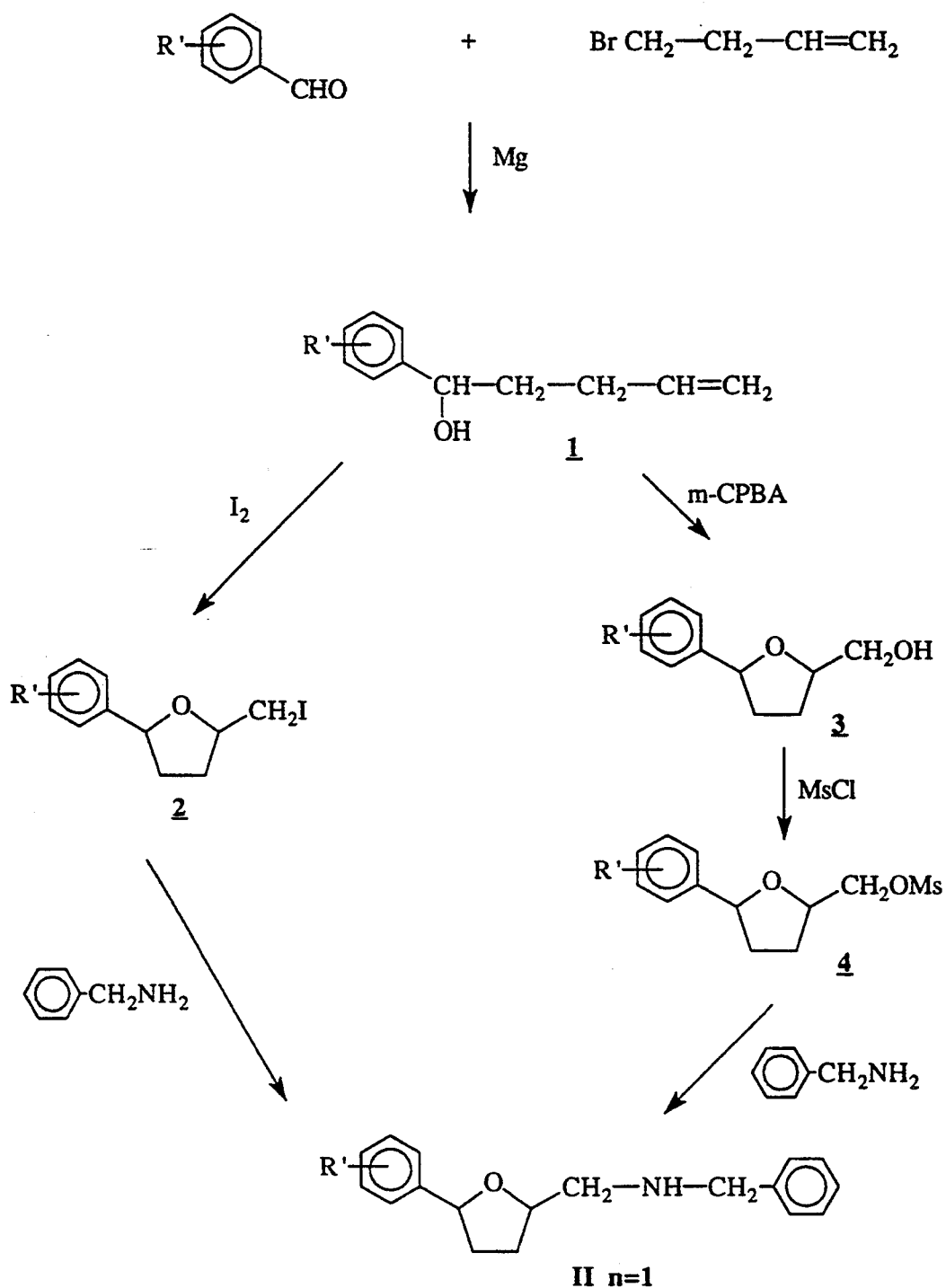
Figure 3:
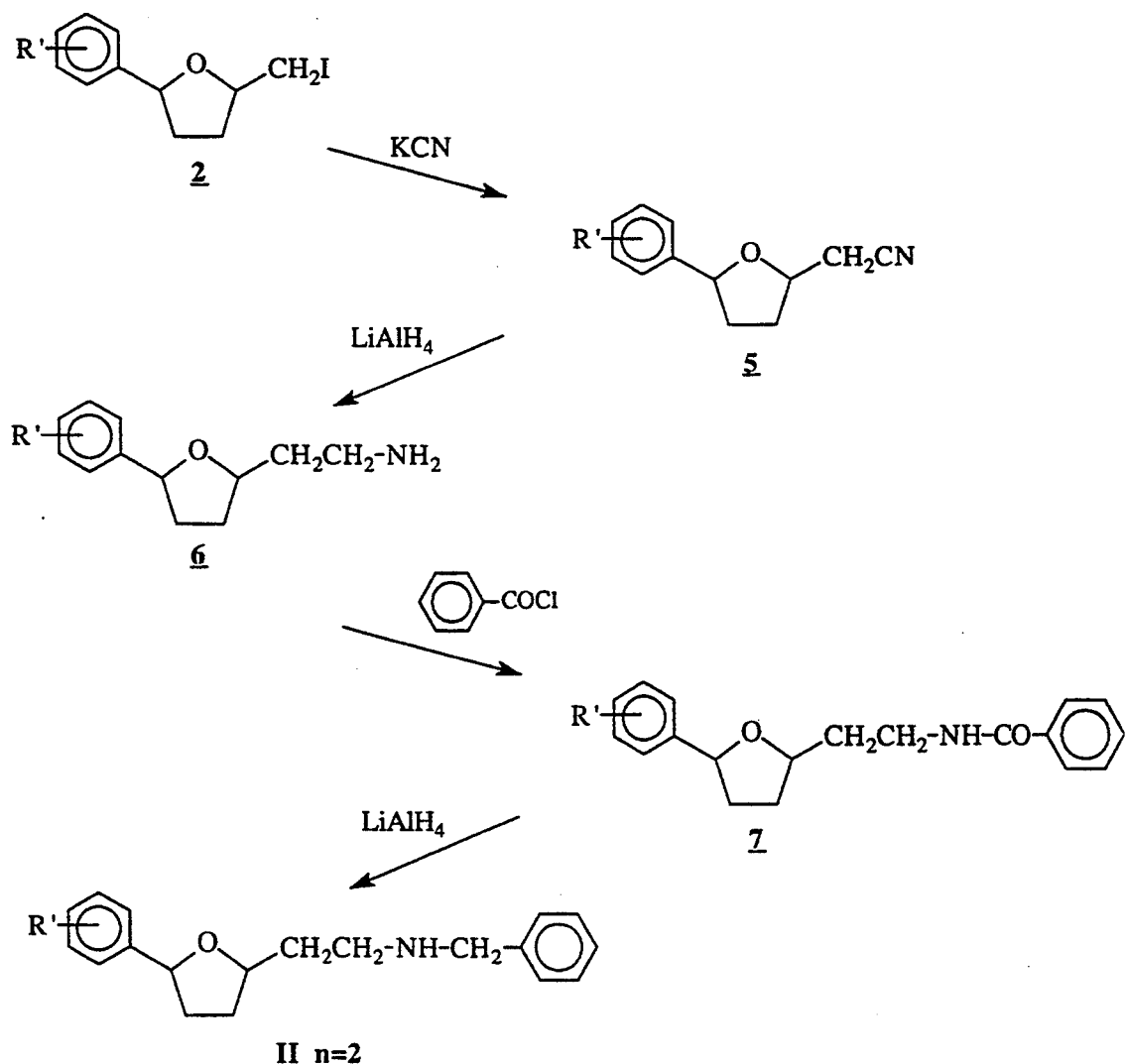
Figure 4:
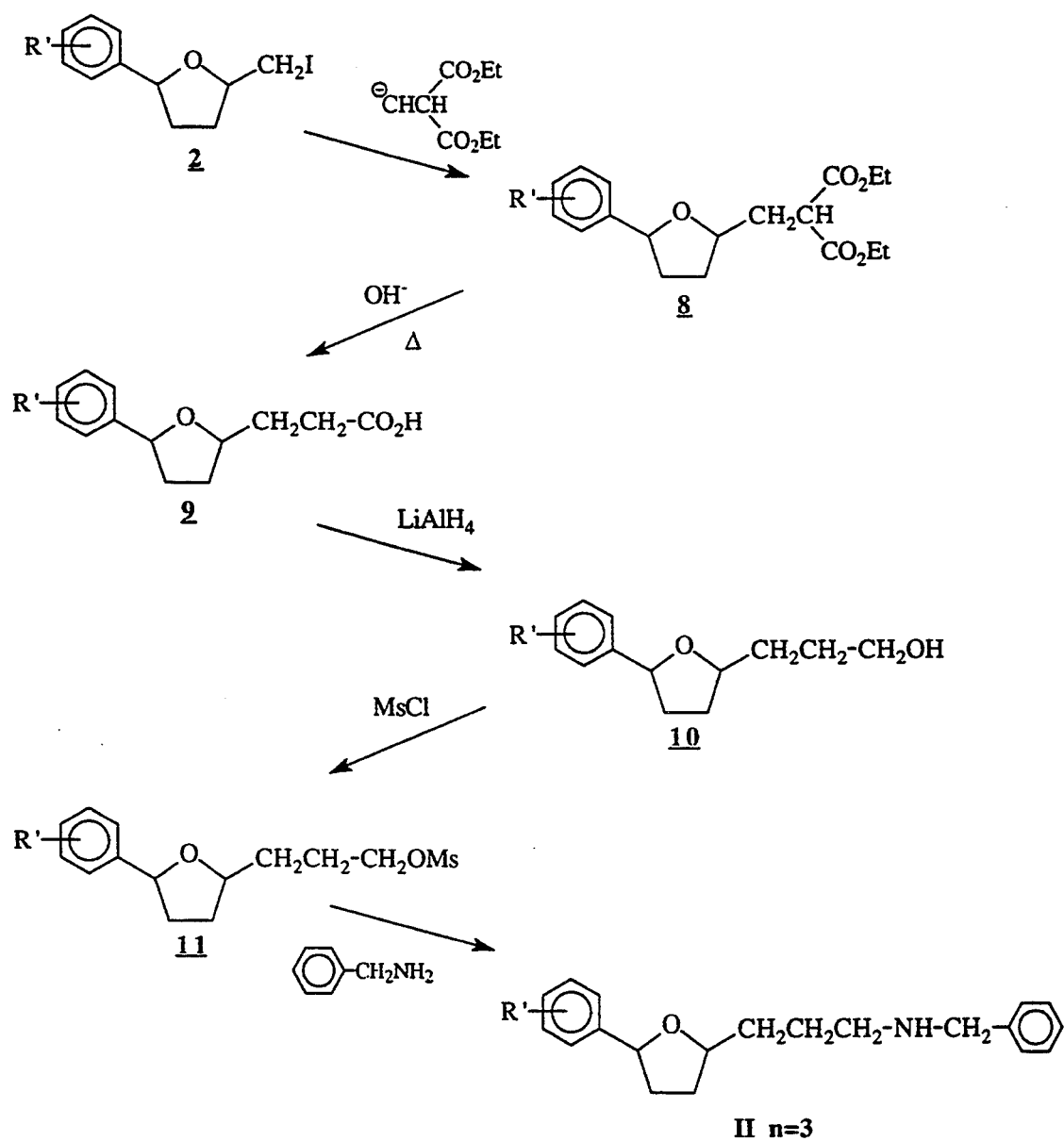
Figure 5:
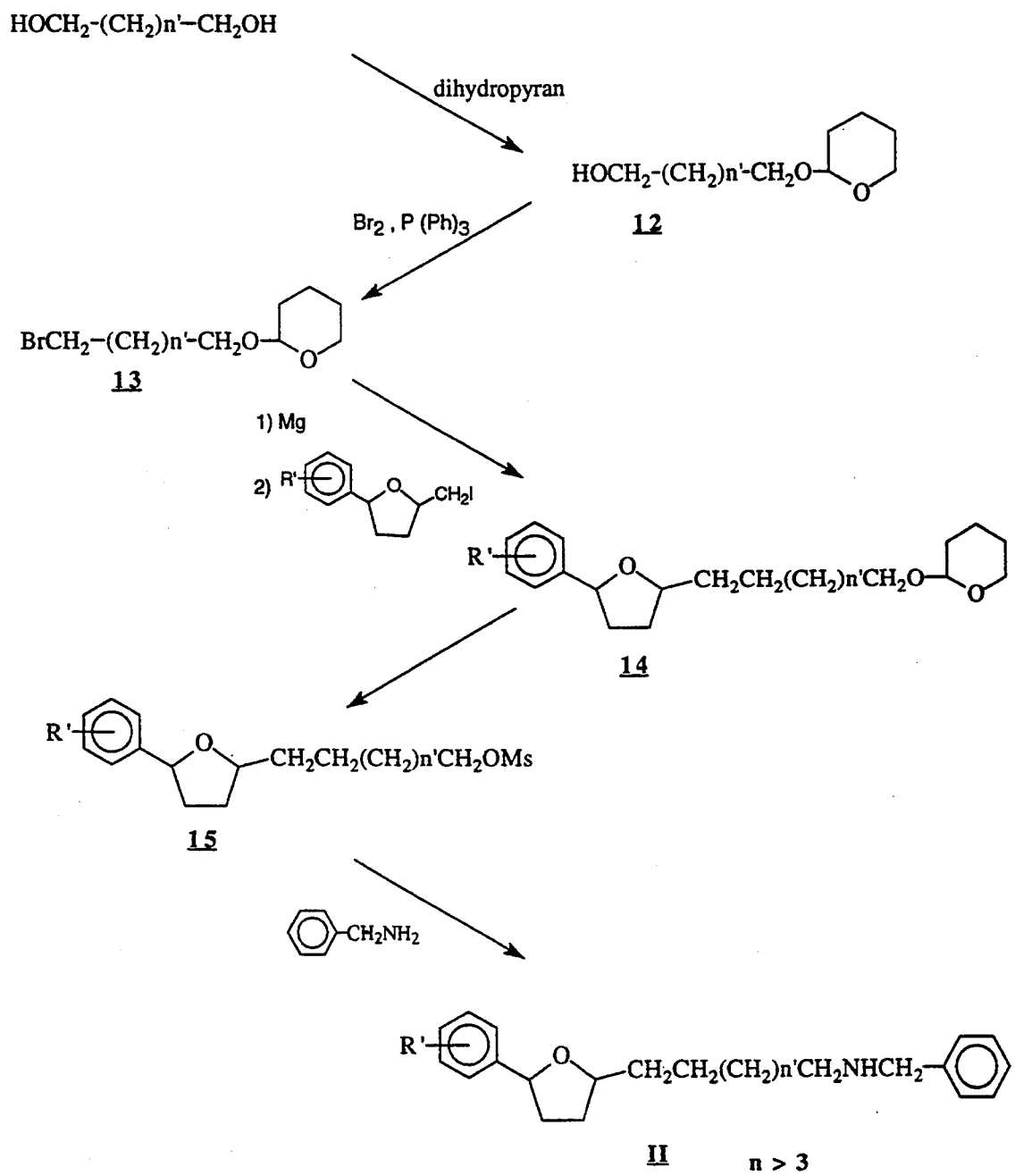
Figure 6:
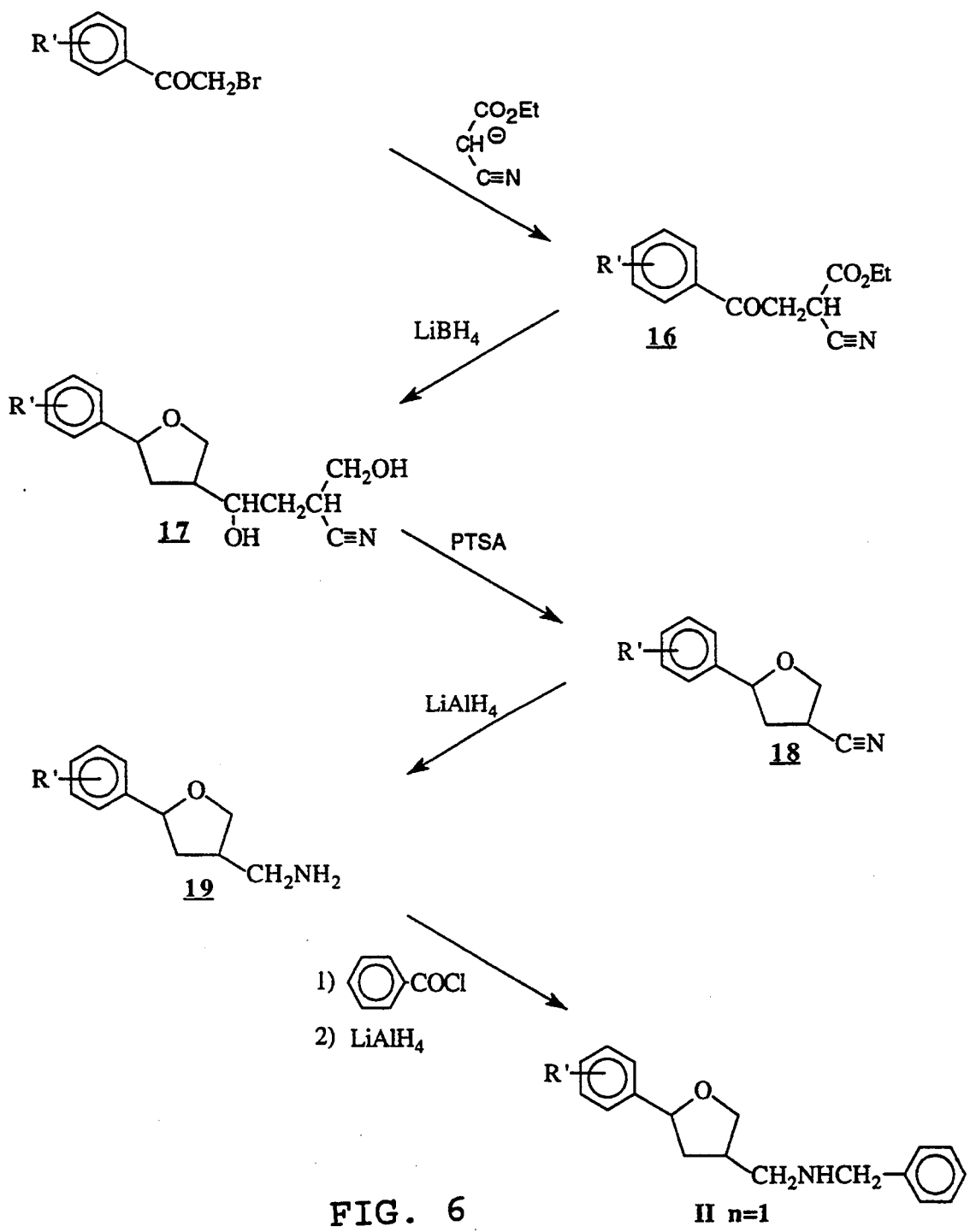

These and other aspects of the present invention may be more fully understood by reference to the following drawings wherein:

FIG. 1, labelled "Reaction Scheme 1", illustrates a preparation process for making a compound of formula I;

FIG. 2, labelled "Reaction Scheme 2", illustrates a preparation process for making a compound of formula II;

FIG. 3, labelled "Reaction Scheme 3", illustrates another preparation process for making a compound of formula II;

FIG. 4, labelled "Reaction Scheme 4", illustrates another preparation process for making a compound of formula II;

FIG. 5, labelled "Reaction Scheme 5", illustrates another preparation process for making a compound of formula II; and FIG. 6, labelled "Reaction Scheme 6", illustrates another preparation process for making a compound of formula II.

The above preparation process may be illustrated by the reaction scheme 1. The cis and trans isomers of compounds of formula I can be obtained either by preparative HPLC of the racemic compounds, or starting from cis/trans isomers of intermediate compounds. These compounds can be separated at different stages of the synthesis, particularly when R stands for an aryl radical. Each of cis and trans compounds is a mixture of two enantiomers which may be obtained by asymmetric synthesis.

The bromocetone III can be obtained by a Fries rearrangement of the phenolic ester of methyl salicylate, followed by bromination of the methyl cetone.

The starting compounds II are new compounds and may be obtained by various ways according to the positions of the substituents and the number of carbon atoms n in the alkyl chain. Benzylamine can be condensed with a cyclopentyl heterocycle substituted with a haloalkyl, or a corresponding mesylate of the alcohol.

The various processes for the preparation of the starting compound II may be illustrated in the enclosed reaction schemes 2 to 6: the reaction schemes 2, 3, 4 and 5 illustrate the synthesis of the starting compound II with a 2,5-disubstitution wherein R stands for an optionally substituted phenyl group and n=1, 2, 3 and n>3 respectively; moreover, the reaction scheme 6 describes the synthesis of the starting compound II with a 2,4-disubstitution wherein R stands for an optionally substituted phenyl group and wherein n=1. Obviously, when R stands for an heteroaryl or an alkyl group, the reaction schemes may be as described in the above reaction schemes 2 to 6.

Finally, the invention provides a pharmaceutical composition comprising of (phenylethyl-$\beta$-ol)amine derivative of the formula I as defined above or a pharmaceutically acceptable salt of such a derivative, in admixture with a pharmaceutically acceptable diluent or carrier.

In the description of the preparation process of any starting compounds II as illustrated below and more specifically when R stands for a substituted phenyl radical, a letter is added, as a superscript, to the number of the compound to simplify and distinguish the different substituents for a given value of n. This convention, followed throughout, is as follows:

| Substitution | $R_1$ | $R_2$ | $R_3$ | $R_4$ | $R_5$ | n | Indice |
|---|---|---|---|---|---|---|---|
| 2,5- | H | H | H | H | H | 1 | a |
| 2,5- | H | $CH_3O$ | $CH_3O$ | $CH_2O$ | H | 1 | b |
| 2,5- | $CH_3O$ | $CH_3O$ | $CH_3O$ | H | H | 1 | c |
| 2,5- | Cl | H | H | H | H | 1 | d |
| 2,5- | H | Cl | H | H | H | 1 | e |
| 2,5- | F | H | H | H | H | 1 | f |
| 2,5- | H | $CH_3O$ | $C_3H_7O$ | $CH_3SO_2$ | H | 1 | g |
| 2,5- | H | H | H | H | H | 2 | h |
| 2,5- | H | $CH_3O$ | $CH_3O$ | $CH_3O$ | H | 2 | i |
| 2,5- | H | $CH_3O$ | $CH_3O$ | $CH_3O$ | H | 3 | j |
| 2,5- | Cl | H | H | H | H | 3 | k |
| 2,5- | H | $CH_3O$ | $CH_3O$ | $CH_3O$ | H | 7 | l |
| 2,4- | H | $CH_3O$ | $CH_3O$ | $CH_3O$ | H | 1 | m |
| 2,4- | Cl | H | H | H | H | 1 | n |

A) Process for the preparation of starting compound II disubstituted in the 2,5-position with n=1
A-1) Process according to reaction scheme 2, for the preparation of compound II wherein R=aryl
5-aryl-5-hydroxy-pentene—group compounds 1

The aldehydes used are in general commercial. For the preparation of compound 1 g, the aldehyde was obtained starting from iodovanilin according to the method of A. S. Thomson (Tetrahedrom Letters, vol. 31, p. 6953, 1990).

The reaction was carried out under argon. To the Grignard reagent obtained from 11 g (80 mmol) of 4-bromobutene and 2 g (80 mmol) of magnesium in tetrahydrofuran (THF), 50 mmol of the appropriate aldehyde in 100 ml of THF was added at room temperature. The stirring was maintained for 1 hour. The reaction mixture was quenched with a 10% aqueous solution of ammonium chloride and extracted with chloroform. After the usual workup, the residue was purified by flash chromatography (light petroleum/ethyl acetate 80:20 then 70:30) to give the alcohol 1 as a viscous product.

Compound $1_a$: $R_f$=0.37 (PE/AcOEt 80:20)
Compound $1_b$: $R_f$=0.43 (PE/AcOEt 50:50)
Compound $1_c$: $R_f$=0.39 (PE/AcOEt 50:50)
Compound $1_d$: $R_f$=0.55 (PE/AcOEt 95:5)
Compound $1_e$: $R_f$=0.35 (PE/AcOEt 90:10)
Compound $1_f$: $R_f$=0.23 (PE/AcOEt 90:10)
Compound $1_g$: $R_f$=0.27 (PE/AcOEt 70:30)

The alcohols all show in $^1$H-NMR (100 MHz, CDCl$_3$, TMS, $\delta$), the following signals: 5.8 (m, 1H, CH=C); 5.0 (t, 2H, C=CH$_2$); 4.6 (t, 1H, C$\underline{H}$OH); 2.1 (2m, 4H, CH$_2$—CH$_2$).

2-aryl-5-iodomethyl-tetrahydrofuran—group compounds 2

A stirred solution of alcohol 1 (71 mmol) in 250 ml of ether and 70 ml of water was cooled to 0° C. 8.9 g (1.5 equivalents) of sodium bicarbornate (NaHCO$_3$), then iodine (27 g, 1.5 equivalents), were added by small portionwise. The mixture was allowed to warm to room temperature and stirred overnight. A solution of sodium thiosulphate (10%) was added. After decantation and washing, the organic phase was dried and concentrated. The thus obtained residue was purified by flash chromatography (light petroleum/ethyl acetate 80:20 then 30:70) to yield the compound 2 as a mixture (yield about 80–85%). In some cases, the cis and trans isomers may be isolated.

Compound $2_a$: $R_f$ (cis)=0.25 $R_f$ (trans)=0.31 (PE/AcOEt 95:5)
Compound $2_b$: $R_f$ (cis)=0.29 $R_f$ (trans)=0.35 (PE/AcOEt 70:30)
Compound $2_c$: $R_f$(rac)=0.39 (PE/AcOEt 80:20)
Compound $2_d$: $R_f$(rac)=0.70 (PE/AcOEt 95:5)
Compound $2_e$: $R_f$ (cis)=0.36 $R_f$ (trans)=0.45 (PE/AcOEt 90:10)
Compound $2_f$: $R_f$(rac)=0.48 (PE/AcOEt 95:5)

IR (cm$^{-1}$): $\nu_{C-O-C}$=1600; $\nu_{OCH3}$=1120 $^1$H-NMR (100 MHz, CDCl$_3$ TMS, $\delta$), characteristic signals: Trans compound: 5.0 (m, 1H, H$_2$); 4.3 (m, 1H, H$_5$); 3.3 (m, 2H CH$_2$I); 2.5–1.7 (m, 4H, CH$_2$—CH$_2$) Cis compound: 4.9 (m, 1H, H$_2$); 4.1 (m, 1H, H$_5$).

When the phenyl radical is substituted by one or more alkylsulphonyl groups, the synthesis of compound II may be performed through the intermediates 3 and 4 as shown in reaction scheme 2.
2-(3'-methoxy-4'-propyloxy-5'-methylsulphonyl-phenyl)-5-hydroxymethyl tetrahydrofuran 3

A solution of anhydrous m-chloroperbenzoic acid (m-CPBA) (14.7 g, 85.2 mmol) in 100 ml of dry dichloromethane was added slowly at 0° C. to a solution of 6.3 g (21.3 mmol) of alcohol 1 g in 200 ml of anhydrous dichloromethane. Stirring was maintained at room temperature overnight, then a saturated solution of sodium thiosulphate was added. After decantation, the organic phase was washed with 1N sodium hydroxide solution, then with water, and dried. After elimination of the solvent, the residue thus obtained was purified on a silica gel column (eluent CH$_2$Cl$_2$/MeOH 98:2) to give a viscous product (5.12 g, yield 70%).

TLC: R$_f$=0.43 (CHCl$_3$/MeOH 95:5) IR (cm$^{-1}$): $\nu_{OH}$=3500; $\nu_{CH3SO2}$=1310 $^1$H NMR (100 MHz, CDCl$_3$, TMS, δ), characteristic signals: 5 (m, 1H, H$_2$); 4.3 (m, 1H, H$_5$); 3.8 (m, 2H, CH$_2$OH); 3.2 (s, 3H, CH$_3$SO$_2$).

Mesylate of 2-(3'-methoxy-4'-propyloxy-5'-methylsulphonyl-phenyl)-5-hydroxymethyl tetrahydrofuran 4

The mesylate 4 was obtained by action of mesyl chloride (MeSO$_2$Cl) on the compound 3, and used without purification in the following step.

TLC: R$_f$=0.54 (CHCl$_3$/MeOH 95:5) $^1$H NMR (100 MHz, CDCl$_3$, TMS, δ): 4.3 (m, 3H, H$_5$ and CH$_2$OMes).

2-aryl-5-benzylaminomethyl-tetrahydrofuran—group compounds II

A solution of benzylamine (4 equivalents) and either the iodide 2 (42 mmol) or the mesylate 4 in 200 ml of anhydrous acetonitrile was refluxed for 5 hours, then evaporated to dryness and taken up in 250 ml of chloroform. After washing with water and drying, the solvent was eliminated. The thus obtained residue was purified by flash chromatography (eluent CHCl$_3$ then CHCl$_3$/MeOH 95:5). The amine was obtained in a yield about 70–75%.

Compound II$_a$: R$_f$(cis)=0.16 R$_f$(trans)=0.22 (AcOEt)
Compound II$_b$: R$_f$ (cis)=0.15 R$_f$ (trans)=0.24 (CHCl$_3$/MeOH 95:5)
Compound II$_c$: R$_f$(rac)=0.28 (CHCl$_3$/MeOH 95:5)
Compound II$_d$: R$_f$(rac)=0.42 (CHCl$_3$/MeOH 90:10)
Compound II$_e$: R$_f$ (cis)=0.26 R$_f$ (trans)=0.25 (CHCl$_3$/MeOH 96:4)
Compound II$_f$: R$_f$(rac)=0.25 (AcOEt)
Compound II$_g$: R$_f$(rac)=0.25 (CHCl$_3$/MeOH 95:5)

IR (cm$^{-1}$): $\nu_{NH}$=3300 $^1$H-NMR (100 MHz, CDCl$_3$, TMS, δ), characteristics signals: Trans compound: 4.9 (t, 1H, H$_2$); 4.3 (m, 1H, H$_5$); 3.8 (d, 2H, NCH$_2$O); 2.7 (d, 2H, CH$_2$N). Cis compound: 4.1 (m, 1H, H$_5$); 2.8 (d, 2H, CH$_2$N).

The enantiomers of compound II(cis) and compound II(trans) may be obtained separately from the corresponding enantiomers 2(cis) and 2(trans) respectively, or 3(cis) and 3(trans) respectively, according to the process as described above (cf. A-1) Preparation of compound II).

Said enantiomers of compound 2 or 3 may be obtained by oxydation of the corresponding alcohol 1 followed by a symmetric reduction and cyclisation. The synthesis of such enantiomers is hereunder illustrated for the compound II$_b$ according to the following successive steps 1' and 2'.

Step 1': 4-(3',4',5'-trimethoxybenzoyl)-butene

A solution of alcohol 1$_b$ (4 mmol) in CH$_2$Cl$_2$ (3 ml) was added dropwise to a mixture of pyridinium chlorochromate (1.5 eq.), sodium acetate (0.04 eq.) and celite (1.5 g) in anhydrous CH$_2$Cl$_2$ (8 ml) at 0° C. under nitrogen atmosphere. The reaction mixture was allowed to room temperature and stirred for about 4 hours (followed by TLC). The insoluble materials were eliminated by filtration. The filtrate was evaporated and the thus obtained residue was purified by flash chromatography (PE/AcOEt 70:30), to give the ketone as a white solid (yield 81%).

Melting point: mp=64° C.; TLC: R$_f$=0.60 (PE/AcOEt 1:1) IR (cm$^{-1}$) $\nu_{CO}$=1680; $\nu_O$=1590 $^1$H-NMR (100 MHz, CDCl$_3$, TMS, δ): 7.3 (s, 2H, O); 5.9 (m, 1H, HC=C); 5.1 (m, 2H, =CH$_2$); 3.9 (s, 9H, OCH$_3$); 3.1 (m, 2H, —C(O)—CH$_2$); 2.5 (q, 2H, CH$_2$—C=)

Step 2': 5-(3'4'5'-trimethoxyphenyl)-5-(−)-hydroxypentene

This step was performed according to Brown H. C., J. Org. Chem. 50, 5446 (1985).

A solution of (−) DIP chloride (β-chlorodiisopinocamphocyl borane) (1.4 eq.) in anhydrous THF (4.5 ml) was added dropwise to a solution of ketone (31.8 mM) in dry THF (45 ml) at 0° C. under stirring. The mixture was allowed to warm to room temperature and stirred overnight. The solvent was evaporated and the thus obtained residue was taken up in diethyl ether and diethylethanolamine (2.2 eq.) was added. After 30 minutes, the insoluble material was filtered off and washed with pentane. Elimination of the filtrate gave a viscous product which was purified by flash chromatography (PE/AcOEt 3:1) to afford the (−) alcohol (yield 65%).

TLC: R$_f$=0.34 (PE/AcOEt 2:1) $[\alpha]_D^{23}$=−32.6 (CHCl$_3$, 0.82 g/100 ml) The (+) alcohol may be obtained according to the process as described above but by using (+) DIPCl instead of (−)-DIPCl.

$[\alpha]_D^{23}$=+30.49 (CHCl$_3$, 0.9 g/100 ml)

The compounds 2$_b$(+) trans and 2$_b$(−) trans may be obtained according to the process as described above (A-1) Preparation of compound 2), starting from the appropriate alcohols 1$_b$(+) trans and 1$_b$(−) trans respectively.

Compound 2$_b$(+) trans: $[\alpha]_D^{23}$=+47.05 (CHCl$_3$, 1.27 g/100 ml)
Compound 2$_b$(−) trans: $[\alpha]_D^{23}$=−46 (CHCl$_3$, 1.8 g/100 ml)

The compounds II$_b$(+) trans and II$_b$(−) trans may be obtained according to the process as described above (cf. A-1: Preparation of compound II), starting from the appropriate compounds 2$_b$(+) trans and 2$_b$(−) trans respectively.

Compound II$_b$(+) trans: $[\alpha]_D^{23}$=+34.545 (CHCl$_3$, 2.2 g/100 ml)
Compound II$_b$(−) trans: $[\alpha]_D^{23}$=−35.1 (CHCl$_3$, 2 g/100 ml)

A-2) Process for the preparation of compound II wherein R=heteroaryl 2-(4'-pyridyl)-5-hydroxy-pentene 1

This compound 1 was obtained as described above and purified by flash chromatography (eluent: AcOEt) to yield a brown oil (60%)

TLC: R$_f$=0.19 (AcOEt) IR (cm$^{-1}$): $\nu_{pyridine}$=1620 and 1590. $^1$H-NMR (100 MHz, CDCl$_3$, TMS, δ): 8.5 (m, 2H, H$_\alpha$N); 7.3 (m, 2H, H aromatic); 5.8 (m, 1H, HC=); 5 (m, 2H, C=CH$_2$); 4.7 (t, 1H, CHOH); 1.9–2.2 (m, 5H, OH and 2CH$_2$).

2-(4'-pyridyl)-5-iodomethyl-tetrahydrofuran 2

This compound was obtained from the corresponding alcohol 1, as described above, and purified by flash chromatography (eluent PE/AcOEt 30:70 then 20:80) (70%).

TLC: R$_f$=0.22 (PE/AcOEt 30:70) IR (cm$^{-1}$): $\nu_{pyridine}$=1600 and 1560; $\nu_{C-O-C}$=1050 $^1$H-NMR (100 MHz, CDCl$_3$, TMS, δ): 8.5 (m, 2H, H$_\alpha$N); 7.3 (m, 2H, 2H aromatic); 5 (m, 1H, H$_2$); 4.3 (m, 1H, H$_5$); 3.4 (m, 2H, CH$_2$I); 2.5–1.7 (m, 4H, CH$_2$—CH$_2$).

2-(4'-pyridyl)-5-benzylaminomethyl-tetrahydrofuran II

This amine was obtained from the corresponding compound 2, as described above, and purified by flash chromatography (eluent CHCl$_3$/MeOH 90:10 then 80:20 and 70:30).

TLC: $R_f = 0.40$ (CHCl$_3$/MeOH 70:30).

A-3) Process for the preparation of compound II wherein R=alkyl

The successive steps for the preparation of the compounds 1, 2 and II respectively, are performed in the same conditions as described above (cf. A-1).

B) Process for the preparation of the starting compound II disubstituted in the 2,5-positions with n=2

B-1) Process according to reaction scheme 3, for the preparation of compound II wherein R=aryl 2-aryl-5-cyanomethyl-tetrahydrofuran—group Compounds 5

A mixture of 2-aryl-5-iodomethyl tetrahydrofuran 2 and potassium cyanide (1.5 equivalents) in 50 ml of dimethylsulphoxide was heated at 80° C. for 3 hours. After cooling, 30 ml of brine was added and the product was extracted with ether. The elimination of the solvent leaves a residue which crystallized or which was purified by chromatography on a silica gel column (eluent PE/AcOEt 50:50 then 40:60). The compounds 5 were obtained in a yield of the order of 70–75%.

Compound $5_h$: $R_f$ (cis)=0.32  $R_f$ (trans)=0.38 (PE/AcOEt 70:30)

Compound $5_i$: $R_f$ (cis)=0.34  $R_f$ (trans)=0.41 (PE/AcOEt 40:60)

Compound $5_h$ cis and $5_i$ cis are viscous compounds.

Compound $5_i$ trans: $m_p$: 98°–100° C.

IR (cm$^{-1}$): $\nu_{C\equiv N}$=2240 $^1$H-NMR (100 MHz, CDCl$_3$, TMS, δ), characteristics signals: Trans compound: 5.1 (m, 1H, H$_2$); 4.5 (m, 1H, H$_5$); 2.7 (m, 2H, CH$_2$CN). Cis compound: 4.9 (m, 1H, H$_2$); 4.3 (m, 1H, H$_5$).

2-aryl-5-(β-amino-ethyl)-tetrahydrofuran—group compounds 6

The reduction of the nitrile 5 was effected with LiAlH$_4$ (3 equivalents) in THF at room temperature. After hydrolysis in basic conditions, the product was extracted with chloroform, dried and the solvent was eliminated. The viscous oil 6 thus obtained was used without purification. Crude yield 80%.

Compound $6_h$: $R_f$ (cis)=0.28  $R_f$ (trans)=0.35 (CHCl$_3$/MeOH/NH$_3$ 80:19:1)

Compound $6_i$: $R_f$ (cis)=0.25  $R_f$ (trans)=0.31 (CHCl$_3$/MeOH/NH$_3$ 80:19:1)

IR (cm$^{-1}$) $\nu_{NH2}$=3350–3300 $^1$H NMR (100 MHz, CDCl$_3$, TMS, δ), principal signals: Trans compound: 4.8 (m, 1H, H$_2$); 4.3 (m, 1H, H$_5$); 2.9 (m, 2H, CH$_2$N). Cis compound: 4.7 (m, 1H, H$_2$); 4.2 (m, 1H, H$_5$).

2-aryl-5-(β-benzoylamino-ethyl)-tetrahydrofuran—group compounds 7

A solution of benzoyl chloride (1 equivalent) in dichloromethane was added slowly at 0° C. to a mixture of the amine 6 and triethylamine (1.1 equivalents) in dichloromethane. Stirring was maintained for 1 hour. After filtration, the solvent was eliminated and the product was purified on a silica gel column (eluent CHCl$_3$/MeOH 98:2 then 97:3) (yield 90%).

Compound $7_h$: $R_f$ (cis)=0.52  $R_f$ (trans)=0.60 (CHCl$_3$/MeOH 97:3)

Compound $7_i$: $R_f$ (cis)=0.50  $R_f$ (trans)=0.57 (CHCl$_3$/MeOH 97:3)

IR (cm$^{-1}$): $\nu_{NH}$=3300; $\nu_{CO}$=1710 $^1$H-NMR (100 MHz, CDCl$_3$, TMS, δ), principal signals: Trans compound: 7.7 (m, 2H, H α to CO); 4.9 (m, 1H, H$_2$); 4.4 (m, 1H, H$_5$); 3.4 (m, 2H, CH$_2$NCO). Cis compound: 4.8 (m, 1H, H$_2$); 4.2 (m, 1H, H$_5$).

2-aryl-5-(β-benzylamino-ethyl)-tetrahydrofuran—group compounds II

Compounds II were obtained by reduction of the amide 7 with LiAlH$_4$ under reflux in THF. The product was purified by chromatography on a silica gel column (eluent CHCl$_3$ then CHCl$_3$/MeOH 95:5) (yield about 70%).

Compound II$_h$: $R_f$ (cis)=0.28  $R_f$ (trans)=0.30 (CHCl$_3$/MeOH 90:10)

Compound II$_i$: $R_f$ (cis)=0.24  $R_f$ (trans)=0.29 (CHCl$_3$/MeOH 90:10)

IR (cm$^{-1}$): $\nu_{NH}$=3300 $^1$H NMR (100 MHz, CDCl$_3$, TMS, δ), principal signals: Trans compound: 4.9 (m, 1H, H$_2$); 4.3 (m, 1H, H$_5$); 3.7 (s, 2H, NCH$_2$O); 2.8 (m, 2H, CH$_2$N) Cis compound: 4.8 (m, 1H, H$_2$); 4.1 (m, 1H, H$_5$).

B-2) Process for the preparation of compound II wherein R=alkyl or heteroaryl

The successive steps for the preparation of compounds 5, 6, 7 and II respectively, may be performed as described above (cf. B-1).

C) Process for the preparation of the starting compound II disubstituted in the 2,5-positions with n=3

C-1) Process according to reaction scheme 4, for the preparation of compound II wherein R=aryl 2-aryl-5-(β-dicarboxyethyl-ethyl)-tetrahydrofuran—group compounds 8

To a suspension of sodium hydride (1.1 equivalents) in 50 ml of anhydrous THF, a solution of ethyl malonate (1 equivalent) was added dropwise. Stirring was maintained for 1 hour at room temperature. 2-aryl-5-iodomethyl-tetrahydrofuran 2 (1 equivalent) dissolved in THF was then added at 0° C., and the mixture was heated under reflux for 30 hours. After cooling, the sodium iodide was filtered off. The solvent was evaporated off and the residue was dissolved in ether and washed. After the usual workup, the residue was purified by flash chromatography (eluent PE/AcOEt 90:10 then 80:20) to afford a colourless viscous oil in a yield about 60%.

Compound $8_j$: $R_f$ (cis)=0.28  $R_f$ (trans)=0.31 (PE/AcOEt 70:30)

Compound $8_k$: $R_f$(rac)=0.51 (PE/AcOEt 70:30)

IR(cm$^{-1}$): $\nu_{CO}$=1740 and 1730. $^1$H-NMR (100 MHz, CDCl$_3$, TMS, δ) principal signals: Trans compound: 4.9 (t, 1H, H$_2$); 4.2 (m, 5H, H$_5$ and 2 OCH$_2$CH$_3$); 3.65 [t, 1H, CH(CO$_2$Et)$_2$]; 1.2 (m, 6H, 2 CH$_3$) Cis compound: 4.8 (t, 1H, H$_2$).

2-aryl-5-(β-carboxy-ethyl)-tetrahydrofuran—group compounds 9

An ethanolic solution of potassium hydroxide (2.05 equivalents) was added slowly to a solution of the diester 8 in ethanol. After 1.5 hours (monosaponification, monitored by TLC), the mixture was refluxed overnight, evaporated to dryness, and taken up in water. The aqueous phase was first extracted with chloroform, then acidified and extracted again with chloroform. The elimination of the solvent gave the diacid (yield 98%). Decarboxylation was obtained by warming the diacid on an oil-bath at 120° C. until the evolution of carbon dioxide ceased (about 1 hour). After cooling, the acid 9 was obtained in a quantitative yield.

IR (cm$^{-1}$): $\nu_{OH\ chelate}$=3400–3300; $\nu_{CO}$=1730 $^1$H-NMR (100 MHz, CDCl$_3$, TMS, δ), principal signals: Trans compound: 5.7 (1H, OH); 4.9 (t, 1H, H$_2$); 4.2 (q, 1H, H$_5$); 2.6 (m, 2H, CH$_2$CO) Cis compound: 7.3 (1H, OH); 4.8 (t, 1H, H$_2$); 4.1 (m, 1H, H$_5$).

2-aryl-5-(γhydroxy)-propyl-tetrahydrofuran—group compounds 10

The reduction of the acid 9 by LiAlH$_4$ (2.5 equivalents), at room temperature, lead to the alcohol 10. The purification was performed on a silica gel column (eluent AcOEt/PE 90:10 then pure AcOEt). Yield: 79%.
Compound 10$_j$: R$_f$ (cis)=0.28 R$_f$ (trans)=0.32 (AcOEt/PE 90:10)
Compound 10$_k$: R$_f$(rac)=0.40 (AcOEt)

IR (cm$^{-1}$): $\nu_{OH}$=3400 $^1$H NMR (100 MHz, CDCl$_3$, TMS, δ) principal signals: Trans compound: 4.9 (t, 1H, H$_2$); 4.2 (m, 1H, H$_5$); 4.1 (m, 2H, CH$_2$OH); 2.8 (1H, OH). Cis compound: 4.8 (t, 1H, H$_2$); 4.1 (m, 3H, H$_5$ and CH$_2$OH); 2.6 (1H, OH).

Mesylate of 2-aryl-5-(γ-hydroxy)-propyl)-tetrahydrofuran—group compounds 11

The mesylate was obtained by action of mesyl chloride in dichloromethane in the presence of triethylamine at room temperature. The product was used in the next step without purification.
Compound 11$_j$: R$_f$(cis)=0.52 R$_f$(trans)=0.49 (AcOEt)
Compound 11$_k$: R$_f$(rac)=0.60 (AcOEt)

IR (cm$^{-1}$): $\nu_{SO2}$=1360 and 1180 $^1$H NMR (100 MHz, CDCl$_3$, TMS, δ), principal signals: Trans compound: 4.9 (t, 1H, H$_2$); 4.2 (m, 3H, H$_5$ and CH$_2$OMs); 2.9 (s, 3H, SO$_2$Me). Cis compound: 4.8 (t, 1H, H$_2$); 4.2 (t, 2H, CH$_2$OMes); 4 (m, 1H, H$_5$'). Specific signals for compound 11$_k$: 5.3 (m, 1H, H$_2$)

2-aryl 5-[N-benzyl δ-amino propyl]tetrahydrofuran—group compounds II

The condensation of the mesylate 11 and the benzylamine was carried out in boiling acetonitrile, according to the process already described (cf. A-1: Process according to scheme 2, step 3). Purification by chromatography on a silica gel column (eluent CHCl$_3$/MeOH 95:5 then 90:10) gave the compound II (approximative yield 60%).
Compound II$_j$: R$_f$ (cis)=0.48 R$_f$ (trans)=0.55 (CHCl$_3$/MeOH 80:20)
Compound II$_k$: R$_f$(rac)=0.51 (CHCl$_3$/MeOH 80:20)

C-2) Process for the preparation of compound II wherein R=alkyl or heteroaryl

The successive steps for the preparation of the compounds 8, 9,10, 11 and II respectively, may be performed as described above (cf. C-1).

D) Process for the preparation of the starting compound II disubstituted in the 2,5-positions with n=7

D-1) Process according to reaction scheme 5, for the preparation of compound II wherein R=aryl 2-(bromohexyl-oxy)tetrahydropyran 13

This compound was obtained by bromation of 2-(hydroxyhexyl-oxy)tetrahydropyran which may be prepared from 1-6 hexanediol and dihydropyran.

$^1$H NMR (100 MHz, CDCl$_3$, TMS, δ), principal signals: 4.6 (m, 1H, O—CH—O); 3.7 (m, 2H, 2H$_\alpha$O); 3.3 (t, 4H, OCH$_2$ and CH$_2$Br); 1.9–1.3 (m, 14H, 7CH$_2$).

2-(3',4',5'-trimethoxyphenyl)-5-[tetrahydropyran-2-oxyhexyl]tetrahydrofuran 14

A mixture of Cu(1)I (0.7 mmol) and compound 2b (trans) in 20 ml of dry THF, was cooled at −40° C., under nitrogen atmosphere. The Grignard reagent prepared from compound 13 in THF was added dropwise. The mixture was stirred at this temperature for 30 minutes, raised to room temperature then refluxed for 6 hours. After usual work up, the product was chromatographed (eluent AcOEt) to yield the compound 14$_l$ trans (60%). R$_f$(trans)=0.51 (AcOEt)

$^1$H NMR (100 MHz, CDCl$_3$, TMS, δ), principal signals: 6.8 (s, 2H, O); 5 (m, 2H, H$_2$); 4.6 (m, 1H, O—CHO); 4.2 (m, 1H, H$_5$); 3.9 (d, 9H, 3CH$_3$O); 3.3 (t, 2H, CH$_2$O); 2.6–1.7 (m, 16H, 2H$_3$, 2H$_4$, 6CH$_2$).

The following successive steps for the preparation of compounds 15 and II, may be performed as described above (cf. reaction scheme 4).

D-2) Process for the preparation of compound II wherein R=alkyl or heteroaryl

The successive steps for the preparation of the compounds 12, 13, 14, 15 and II respectively, may be performed as described above (cf. D-1).

E) Process for the preparation of the starting compound II disubstituted in the 2,4-positions with n=1

E-1) Process according to reaction scheme 6, for the preparation compound II wherein R=aryl Ethyl 4-aryl-4-oxo-2-cyano-butyrate—group compounds 16

To a suspension of sodium hydride (1.1 equivalents) in anhydrous THF, 5.8 g (52 mmol) of ethyl cyanoacetate, in 100 ml of THF, was added dropwise. The mixture was stirred 30 minutes more then cooled to 0° C. and a solution of 52 mmol of bromomethyl-aryl-ketone in 150 ml of THF was added slowly. The mixture was allowed to warm to room temperature then refluxed for 1 hour. A hydrolysis followed by an extraction with chloroform lead, after the usual workup, to a product. A purification by silica gel column chromatography (eluent PE/AcOEt 60:40) afforded compound 16.
Compound 16$_m$: R$_f$=0.5 (PE/AcOEt 50:50)
Compound 16$_n$: R$_f$=0.62 (PE/AcOEt 50:50)

IR (cm$^{-1}$): $\nu_{CN}$=2240; $\nu_{CO2Et}$=1730; $\nu_{CO}$=1680. $^1$H-NMR (100 MHz, CDCl$_3$, TMS, δ), main signals: 4.3 (q, 2H, OCH$_2$CH$_3$); 4.1 (t, 1H, CH); 3.6 (m, 2H, COCH$_2$); 1.3 (t, 3H, CH$_3$).

4-aryl-2-cyano-1,4-dihydroxy-butane—group compounds 17

Compound 17 was obtained by reducing the ketone and ester moieties of the compound 16, with LiBH$_4$ (2.2 equivalents) in THF at room temperature. After the usual treatments, a purification on a silica gel column (eluent AcOEt/PE 80:20 then 90:10 then AcOEt) provided the diol 17 (yield 75%).
Compound 17$_m$: R$_f$(rac)=0.31 (AcOEt)
Compound 17$_n$: R$_f$(rac)=0.39 (AcOEt)

IR (cm$^{-1}$): $\nu_{OH}$=3400; $\nu_{CN}$=2240 $^1$H NMR (100 MHz, CDCl$_3$, TMS, δ), main signals: 5.35 (t, 2H, CHOH); 3.8 (m, 2H, CH$_2$OH); 3.15 (m, 1H, CHCN); 2.7 (2H, 2OH exchangeable with D$_2$O); 1.9 (m, 2H, CH$_2$CHCN)

4-aryl-2-cyano-tetrahydrofuran—group compounds 18

A mixture of diol 17 (28 mmol) and 0.2 g of p-toluenesulphonic acid in 100 ml of anhydrous benzene was refluxed in an apparatus fitted with a Dean and Stark trap, for 5 hours. After elimination of the solvent, the residue was purified by flash chromatography (eluent PE/AcOEt 60:0) to afford compound 18 as cis, trans isomers (yield 75–78%).
Compound 18$_m$: R$_f$ (cis)=0.36 R$_f$ (trans)=0.41 (PE/AcOEt 50:50)
Compound 18$_n$: R$_f$ (cis)=0.46 R$_f$ (trans)=0.58 (PE/AcOEt 50:50)

IR (cm$^{-1}$) $\nu_{CN}$=2240; $\nu_{C-O-C}$=1010 $^1$H NMR (100 MHz, CDCl$_3$, TMS, δ) Trans compound: 5 (t, 1H, H$_2$); 4.4 and 4.1 (2m, 2H, 2H$_5$); 3.3 (m, 1H, H$_4$); 2.6 and 2.2 (2m, 2H, H$_3$) Cis compound: 4.8 (t, 1H, H$_2$); 4.3 and 4.1 (2m, 2H, 2H$_5$); 2.7 and 2.1 (2m, 2H, H$_3$).

4-aryl-2-aminomethyl-tetrahydrofuran—group compounds 19

The reduction of the nitrile 18 with LiAlH$_4$ lead to the amine 19 (yield 89%).

Compound 19$_m$: R$_f$ (rac)=0.49 (CHCl$_3$/MeOH/NH$_3$, 80:19:1)

Compound 19$_n$: R$_f$ (rac)=0.51 (CHCl$_3$/MeOH/NH$_3$, 80:19:1)

IR (cm$^{-1}$) $\nu_{NH2}$=3400 and 3350 $^1$H NMR (100 MHz, CDCl$_3$, TMS, δ) (mixture): 4.85 (m, 1H, H$_2$); 4.3-3.6 (m, 4H, 2H$_5$, CH$_2$N); 2.7 (m, 1H, H$_4$); 2.4 and 2 (2m, 2H, H$_3$); 1.5 (2H, NH$_2$ exchangeable with D$_2$O).

4-aryl-2-(N-benzyl-aminomethyl)-tetrahydrofuran—group compound II

The amine 19 was condensed with benzoyl chloride and the thus obtained amide was reduced with LiAlH$_4$. The product II thus obtained was purified on a silica gel column (eluent CHCl$_3$/MeOH 98:2 then 95:5).

Compound II$_m$: R$_f$(rac)=0.38 (CHCl$_3$/MeOH 98:2)

Compound II$_n$: R$_f$(rac)=0.40 (CHCl$_3$/MeOH 98:2)

IR (cm$^{-1}$): $\nu_{NH}$=3300 $^1$H NMR (100 MHz, CDCl$_3$, TMS, δ): 7.3 (m, 5H, O); 4.8 (m, 1H, H$_2$); 4.3-3.5 (m, 6H, 2H$_5$, CH$_2$NCH$_2$); 2.6 (1H, NH); 2.5-2 (2m, 2H, H$_3$).

E-2) Process for the preparation of compound II wherein R=alkyl or heteroaryl

The successive steps for the preparation of the compounds 16, 17, 18, 19 and II respectively, may be performed as described above (cf. E-1).

The following Examples illustrate the invention.

Example 1

2-phenyl-5-[N-[β-(3'-hydroxymethyl-4'-hydroxy-phenyl)-β-hydroxy-ethyl]aminomethyl]-tetrahydrofuran Compound I, with a 2,5-disubstitution in which n=1 and R=phenyl

Step 1

2-phenyl-5-[N-benzyl-N-(3'-methoxycarbonyl-4'-hydroxy-phenacyl)]-aminomethyltetrahydrofuran IV A solution of methyl-5-bromoacetyl salicylate III (1.05 equivalents) in 100 ml of anhydrous acetonitrile was added dropwise to a solution of the appropriate amine II (28 mmol) and triethylamine (1.1 equivalents) in 120 ml of acetonitrile. The mixture was stirred at room temperature 2.5 hours more, then concentrated to dryness and taken up in chloroform. After the usual workup, the residue was purified by flash chromatography (PE/AcOEt 90:10 to 70:30) to yield compound IV (71%). M=473 g TLC: R$_f$(rac)=0.47 (PE/AcOEt 60:40) IR (cm$^{-1}$): $\nu_{OH}$=3100; $\nu_{CO2Me}$=1690; $\nu_{CO}$=1670 $^1$H-NMR (100 MHz, CDCl$_3$, TMS, δ), characteristics signals: Trans compound: 11.2 (1H, OH); 8.5 (d, 1H, H$_2$); 8.1 (2d, 1H, H$_6$); 7.3 (m, 5H, O); 6.9 (d, 1H, H$_5$'); 4.8 (t, 1H, H$_2$); 4.4 (m, 1H, H$_5$); 3.85 (m, 7H, CO$_2$Me, NCH$_2$CO, NCH$_2$O); 2.8 (d, 2H, CH$_2$N). Cis compound: 4.2 (m, 1H, H$_5$); 2.9 (d, 2H, CH$_2$N).

Step 2

2-phenyl-5-[[N-benzyl-N-[β-hydroxy-β-(3'-hydroxymethyl-4'-hydroxy-phenyl)-ethyl]-aminomethyl]-tetrahydrofuran V To a suspension of LiAlH$_4$ (3 equivalents) in 50 ml of anhydrous tetrahydrofuran (THF), cooled to 0° C. under nitrogen atmosphere, was added dropwise a solution of the compound IV as obtained above (16 mmol) in 100 ml of THF. The mixture was allowed to warm to room temperature and stirred 1.5 hours more. The reaction was quenched in basic medium. After extraction with chloroform and usual workup, the residue was purified by chromatography (AcOEt/PE 80:20 then AcOEt) to yield V (77%). M=447 g TLC: R$_f$(rac)=0.24 (CH$_2$Cl$_2$/MeOH 95:5) $^1$H-NMR (100 MHz, CDCl$_3$, TMS, δ), characteristics signals: Trans compound: 11.1 (1H, OH); 4.9 (t, 1H, H$_2$); 4.5 (m, 3H, H$_5$ and CH$_2$OH); 2.8-2.7 (m, 4H, CH$_2$NCH$_2$). Cis compound: 4.8-4.5 (m, 4H, H$_2$, H$_5$ and CH$_2$OH).

Step 3

2-phenyl-5-[N-[β-(3'-hydroxymethyl-4'-hydroxy-phenyl)-β-hydroxy-ethyl]aminomethyl]-tetrahydrofuran I The compound I was obtained by hydrogenolysis of the compound V as obtained above, in methanol, in the presence of Pd/C 10%, under a pressure of 2.7 bar for 2-4 hours. The catalyst was filtered off and the solvent eliminated. The product was purified by chromatography on a silica gel column (eluent CHCl$_3$/MeOH 95:5 then 90:10) to yield compound I (73%). Purity was checked by thin layer chromatography (TLC) and HPLC. M=343 g TLC: R$_f$(rac)=0.16 (CHCl$_3$/MeOH 80:20). HPLC: reverse phase column C$_{18}$-5μ, Nucleosil 125, CFCC 3F 10386; 150×4.6 mm: T$_R$min=12.5 (eluent MeOH/H$_2$O/TFA 25:75:0.5%—Flow rate 1 ml/min) IR (cm$^{-1}$), general absorption bands: $\nu_{OH}$ and $\nu_{NH}$=3400-3300; $\nu_O$=1590; $\nu_{C\ OH}$=1220; $\nu_{C-O-C}$=1040 $^1$H-NMR: δ (ppm) (cf table 1)

The fumarate salt was prepared by heating, under reflux for 5 minutes, an equimolar mixture of the compound I as obtained above and fumaric acid in absolute ethanol. Melting point (°C.): mp (rac)=98

Example 2

2-(3',4',5'-trimethoxyphenyl)-5-[N-[β-(3'-hydroxymethyl-4'-hydroxy-phenyl)-β-hydroxy-ethyl]-aminomethyl]-tetrahydrofuran Compound I, with a 2,5-disubstitution in which n=1 and R=3,4,5-trimethoxyphenyl

Step 1

2-(3',4',5'-trimethoxyphenyl)-5-[N-benzyl-N-(3'-methoxycarbonyl-4'-hydroxy-phenacyl)]-aminomethyl tetrahydrofuran IV The compound IV was obtained according to the process as described above (cf. example 1, step 1), starting from the appropriate starting compound II (71%).

M=549 g TLC: R$_f$ (cis)=0.42 R$_f$ (trans)=0.38 (PE/AcOEt 60:40) IR (cm$^{-1}$): $\nu_{OH}$=3100; $\nu_{CO2Me}$=1690; $\nu_{CO}$=1670 $^1$H-NMR (100 MHz, CDCl$_3$, TMS, δ), characteristics signals: Trans compound: 11.2 (1H, OH); 8.5 (d, 1H, H$_2$'); 8.1 (2d, 1H, H$_6$); 7.3 (m, 5H, O); 6.9 (d, 1H, H$_5$'); 4.8 (t, 1H, H$_2$); 4.4 (m, 1H, H$_5$); 3.85 (m, 7H, CO$_2$Me, NCH$_2$CO, NCH$_2$O); 2.8 (d, 2H, CH$_2$N). Cis compound: 4.2 (m, 1H, H$_5$); 2.9 (d, 2H, CH$_2$N).

Step 2

2-(3',4',5'-trimethoxyphenyl)-5-[[N-benzyl-N-[β-hydroxy-β-(3'-hydroxymethyl-4'-hydroxy-phenyl)-ethyl]-aminomethyl]-tetrahydrofuran V The compound V was obtained according to the process as described above (cf. example 1, step 2), starting from the compound IV as obtained above (77%).

M=523 g TLC: R$_f$ (cis)=0.41 R$_f$ (trans)=0.43 (AcOEt) $^1$H-NMR (100 MHz, CDCl$_3$, TMS, δ), characteristics signals: Trans compound: 11.1 (1H, OH); 4.9 (t, 1H, H$_2$); 4.5 (m, 3H, H$_5$ and CH$_2$OH); 2.8–2.7 (m, 4H, CH$_2$NCH$_2$). Cis compound: 4.8–4.5 (m, 4H, H$_2$, H$_5$ and CH$_2$OH).

Step 3

2-(3′,4′,5′-trimethoxyphenyl)-5-[N-[β-(3′-hydroxymethyl-4′-hydroxy-phenyl)-β-hydroxy-ethyl]-aminomethyl]-tetrahydrofuran I The compound I was obtained according to the process as described above (cf. example 1, step 3), starting from the compound V as obtained above (71%).

M=433 g TLC: R$_f$ (cis)=0.25 R$_f$ (trans)=0.21 (CHCl$_3$/MeOH 80:20) HPLC: reverse phase column C$_{18}$-5μ, Nucleosil 125, CFCC 3F 10386; 150×4.6 mm: T$_R$min (cis)=12.4; T$_R$min (trans)=7.2 (eluent MeOH/H$_2$O/TFA 50:50:0.5%—Flow rate 0.5 ml/min) IR (cm$^{-1}$), general absorption bands: $v_{OH}$ and $v_{NH}$=3400–3300; $v_O$=1590; $v_{C\ OH}$=1220; $v_{C-O-C}$=1040; $v_{OCH_3}$=1130 $^1$H-NMR: δ (ppm) (cf table 1) Compound I trans(+) [α]$_D^{23}$=+32.147 (CHCl$_3$, 0.871 g/100 ml) Compound I trans(−) [α]$_D^{23}$=−34.2 (CHCl$_3$, 0.92 g/100 ml)

The fumarate salt was prepared by using the compound I as obtained above and fumaric acid. Melting points (°C.): mp (cis)=111-113 mp (trans)=124

Example 3

2-(2′,3′,4′-trimethoxyphenyl)-5-[N-[β-(3′-hydroxymethyl-4′-hydroxy-phenyl)-β-hydroxy-ethyl]-aminomethyl]-tetrahydrofuran Compound I, with a 2,5-disubstitution in which n=1 and R=2,3,4-trimethoxyphenyl

Step 1

2-(2′,3′,4′-trimethoxyphenyl)-5-[N-benzyl-N-(3′-methoxycarbonyl-4′-hydroxy-phenacyl)]-aminomethyl-tetrahydrofuran IV The compound IV was obtained according to the process as described above (cf. example 1, step 1), starting from the appropriate starting compound II (76%).

M=549 g TLC: R$_f$(rac)=0.25 (PE/AcOEt 70:30) IR (cm$^{-1}$): $v_{OH}$=3100; $v_{CO_2Me}$=1690; $v_{CO}$=1670 $^1$H-NMR (100 MHz, CDCl$_3$, TMS, δ), characteristics signals: Trans compound: 11.2 (1H, OH); 8.5 (d, 1H, H$_{2′}$); 8.1 (2d, 1H, H$_6$); 7.3 (m, 5H, O); 6.9 (d, 1H, H$_{5′}$); 4.8 (t, 1H, H$_2$); 4.4 (m, 1H, H$_5$); 3.85 (m, 7H, CO$_2$Me, NCH$_2$CO, NCH$_2$O); 2.8 (d, 2H, CH$_2$N). Cis compound: 4.2 (m, 1H, H$_5$); 2.9 (d, 2H, CH$_2$N).

Step 2

2-(2′,3′,4′-trimethoxyphenyl)-5-[N-benzyl-N-[β-hydroxy-β-(3′-hydroxymethyl-4′-hydroxy-phenyl)-ethyl]-aminomethyl]-tetrahydrofuran V The compound V was obtained according to the process as described above (cf. example 1, step 2), starting from the compound IV as obtained above (80%).

M=523 g TLC: R$_f$ (rac)=0.40 (CH$_2$Cl$_2$/MeOH 10:90) $^1$H-NMR (100 MHz, CDCl$_3$, TMS, δ), characteristics signals: Trans compound: 11.1 (1H, OH); 4.9 (t, 1H, H$_2$); 4.5 (m, 3H, H$_5$ and CH$_2$OH); 2.8–2.7 (m, 4H, CH$_2$NCH$_2$). Cis compound: 4.8–4.5 (m, 4H, H$_2$, H$_5$ and CH$_2$OH).

Step 3

2-(2′,3′,4′-trimethoxyphenyl)-5-[N-[β-(3′-hydroxymethyl-4′-hydroxy-phenyl)-β-hydroxy-ethyl]-aminomethyl]-tetrahydrofuran I The compound I was obtained according to the process as described above (cf. example 1, step 3), starting from the compound V as obtained above. The cis and trans isomers are separated by preparative HPLC (70%). M=433 g TLC: R$_f$(cis)=0.37 R$_f$(trans)=0.32 (CHCl$_3$/MeOH 80:20) HPLC: reverse phase column C$_{18}$-5μ, Nucleosil 125, CFCC 3F 10386; 150×4.6 mm: T$_R$min (cis)=47; T$_R$min (trans)=45 (eluent MeOH/H$_2$O/TFA 25:75:0.5%—Flow rate 1 ml/min) IR (cm$^{-1}$), general absorption bands: $v_{OH}$ and $v_{NH}$=3400–3300; $v_O$=1590; $v_{COH}$=1220; $v_{C-O-C}$=1040; $v_{OCH_3}$=1130 $^1$H-NMR: δ (ppm) (cf table 1)

The fumarate salt was prepared by using the compound I as obtained above and fumaric acid. Melting point (°C.): mp (trans)=145

Example 4

2-(2′-chlorophenyl)-5-[N-[β-(3′-hydroxymethyl-4′-hydroxy-phenyl)-β-hydroxy-ethyl]-aminomethyl]-tetrahydrofuran Compound I, with a 2,5-disubstitution in which n=1 and R=2-chlorophenyl

Step 1

2-(2′-chlorophenyl)-5-[N-benzyl-N-*3′-methoxycarbonyl-4′-hydroxy-phenacyl)]-aminomethyl-tetrahydrofuran IV The compound IV was obtained according to the process as described above (cf. example 1, step 1), starting from the appropriate starting compound II (69%).

M=493.5 g TLC: R$_f$ (cis)=0.26 R$_f$ (trans)=0.21 (PE/AcOEt 80:20) IR (cm$^{-1}$): $v_{OH}$=3100; $v_{CO_2Me}$=1690; $v_{CO}$=1670 $^1$H-NMR (100 MHz, CDCl$_3$, TMS, δ), characteristics signals: Trans compound: 11.2 (1H, OH); 8.5 (d, 1H, H$_{2′}$); 8.1 (2d, 1H, H$_6$); 7.3 (m, 5H, O); 6.9 (d, 1H, H$_{5′}$); 4.8 (t, 1H, H$_2$); 4.4 (m, 1H, H$_5$); 3.85 (m, 7H, CO$_2$Me, NCH$_2$CO, NCH$_2$O); 2.8 (d, 2H, CH$_2$N). Cis compound: 4.2 (m, 1H, H$_5$); 2.9 (d, 2H, CH$_2$N).

Step 2

2-(2′-chlorophenyl)-5-[[N-benzyl-N-[β-hydroxy-β-(3′-hydroxymethyl-4′-hydroxyphenyl)ethyl]-aminomethyl]-tetrahydrofuran V The compound V was obtained according to the process as described above (cf. example 1, step 2), starting from the compound IV as obtained above (75%).

M=467.5 g TLC: R$_f$ (cis)=0.41 R$_f$ (trans)=0.44 (PE/AcOEt 10:90) $^1$H-NMR (100 MHz, CDCl$_3$, TMS, δ), characteristics signals: Trans compound: 11.1 (1H, OH); 4.9 (t, 1H, H$_2$); 4.5 (m, 3H, H$_5$ and CH$_2$OH); 2.8–2.7 (m, 4H, CH$_2$NCH$_2$). Cis compound: 4.8–4.5 (m, 4H, H$_2$, H$_5$ and CH$_2$OH).

Step 3

2-(2′-chlorophenyl)-5-[N-[β-(3′-hydroxymethyl-4′-hydroxy-phenyl)-β-hydroxyethyl]-aminomethyl]-tetrahydrofuran I The compound I was obtained according to the process as described above (cf. example 1, step 3), starting from the compound V as obtained above in presence of PtO$_2$ instead of Pt/C (73%). M=377.5 g TLC: R$_f$(cis)=0.18 R$_f$(trans)=0.15 (CHCl$_3$/MeOH 80:20) HPLC: reverse phase column C$_{18}$-5μ, Nucleosil 125, CFCC 3F 10386; 150×4.6 mm: T$_R$min (cis)=38; T$_R$min (trans)=35 (eluent MeOH/H$_2$O/TFA 25:75:0.5%—Flow rate 1 ml/min) IR (cm$^{-1}$), general absorption bands: $\nu_{OH}$ and $\nu_{NH}=3400-3300$; $\nu_O=1590$; $\nu_{C\ OH}=1220$; $\nu_{C-O-C}=1040$ $^1$H-NMR: δ (ppm) (cf table 1)

The fumarate salt was prepared by using the compound I as obtained above and fumaric acid. Melting point (°C.): mp (cis)=90 mp (trans)=80

Example 5

2-(3'-chlorophenyl)-5-[N-[β-(3'-hydroxymethyl-4'-hydroxy-phenyl)-β-hydroxy-ethyl]-aminomethyl]-tetrahydrofuran Compound I, with a 2,5-disubstitution in which n=1 and R=3-chlorophenyl

Step 1

2-(3'-chlorophenyl)-5-[N-benzyl-N-(3'-methoxycarbonyl-4'-hydroxy-phenacyl)]-aminomethyl-tetrahydrofuran IV The compound IV was obtained according to the process as described above (cf. example 1, step 1), starting from the appropriate starting compound II (79%).

M=493.5 g TLC: R$_f$ (cis)=0.23 R$_f$ (trans)=0.29 (PE/AcOEt 80:20) IR (cm$^{-1}$): $\nu_{OH}$=3100; $\nu_{CO2Me}$=1690; $\nu_{CO}$=1670 $^1$H-NMR (100 MHz, CDCl$_3$, TMS, δ), characteristics signals: Trans compound: 11.2 (1H, OH); 8.5 (d, 1H, H$_{2'}$); 8.1 (2d, 1H, H$_6$); 7.3 (m, 5H, O); 6.9 (d, 1H, H$_{5'}$); 4.8 (t, 1H, H$_2$); 4.4 (m, 1H, H$_5$); 3.85 (m, 7H, CO$_2$Me, NCH$_2$CO, NCH$_2$O); 2.8 (d, 2H, CH$_2$N). Cis compound: 4.2 (m, 1H, H$_5$); 2.9 (d, 2H, CH$_2$N).

Step 2

2-(3'-chlorophenyl)-5-[[N-benzyl-N-[β-hydroxy-β-(3'-hydroxymethyl-4'-hydroxyphenyl)-ethyl]-aminomethyl]-tetrahydrofuran V The compound V was obtained according to the process as described above (cf. example 1, step 2), starting from the compound IV as obtained above. M=467.5 g TLC: R$_f$ (cis)=0.35 R$_f$ (trans)=0.33 (PE/AcOEt 20:80) $^1$H-NMR (100 MHz, CDCl$_3$, TMS, δ), characteristics signals: Trans compound: 11.1 (1H, OH); 4.9 (t, 1H, H$_2$); 4.5 (m, 3H, H$_5$ and CH$_2$OH); 2.8–2.7 (m, 4H, CH$_2$NCH$_2$). Cis compound: 4.8–4.5 (m, 4H, H$_2$, H$_5$ and CH$_2$OH).

Step 3

2-(3'-chlorophenyl)-5-[N-[β-(3'-hydroxymethyl-4'-hydroxy-phenyl)-β-hydroxyethyl]-aminomethyl]-tetrahydrofuran I The compound I was obtained according to the process as described above (cf. example 1, step 3), starting from the compound V as obtained above in presence of PtO$_2$ instead of Pd/C (73%). M=377.5 g TLC: R$_f$(cis)=0.17 R$_f$(trans)=0.14 (CHCl$_3$/MeOH 80:20) HPLC: reverse phase column C$_{18}$-5μ, Nucleosil 125, CFCC 3F 10386; 150×4.6 mm: T$_R$min (cis)=35; T$_R$min (trans)=32.5 (eluent MeOH/H$_2$O/TFA 25:75:0.5%—Flow rate 1 ml/min) IR (cm$^{-1}$), general absorption bands: $\nu_{OH}$ and $\nu_{NH}$=3400–3300; $\nu_O$=1590; $\nu_{C\ OH}$=1220; $\nu_{C-O-C}$=1040 $^1$H-NMR: δ (ppm) (cf table 1)

The fumarate salt was prepared by using the compound I as obtained above and fumaric acid. Melting point (°C.): mp (cis)=72 mp (trans)=84

Example 6

2-(2'-fluorophenyl)-5-[N-[β-(3'-hydroxymethyl-4'-hydroxy-phenyl)-β-hydroxy-ethyl]-aminomethyl]-tetrahydrofuran Compound I, with a 2,5-disubstitution in which n=1 and R=2-fluorophenyl.

Step 1

2-(2'-fluorophenyl)-5-[N-benzyl-N-(3'-methoxycarbonyl-4'-hydroxy-phenacyl)]-aminomethyl]-tetrahydrofuran IV The compound IV was obtained according to the process as described above (cf. example 1, step 1), starting from the appropriate starting compound II (78%).

M=477.5 g TLC: R$_f$(rac)=0.34 (PE/AcOEt 80:20) IR (cm$^{-1}$): $\nu_{OH}$=3100; $\nu_{CO2Me}$=1690; $\nu_{CO}$=1670 $^1$H-NMR (100 MHz, CDCl$_3$, TMS, δ), characteristics signals: Trans compound: 11.2 (1H, OH); 8.5 (d, 1H, H$_{2'}$); 8.1 (2d, 1H, H$_6$); 7.3 (m, 5H, O); 6.9 (d, 1H, H$_{5'}$); 4.8 (t, 1H, H$_2$); 4.4 (m, 1H, H$_5$); 3.85 (m, 7H, CO$_2$Me, NCH$_2$CO, NCH$_2$O); 2.8 (d, 2H, CH$_2$N). Cis compound: 4.2 (m, 1H, H$_5$); 2.9 (d, 2H, CH$_2$N).

Step 2

2-(2'-fluorophenyl)-5-[[N-benzyl-N-β-hydroxy-β-(3'-hydroxymethyl-4'-hydroxy-phenyl)ethyl-aminomethyl]-tetrahydrofuran V The compound V was obtained according to the process as described above (cf. example 1, step 2), starting from the compound IV as obtained above (78%).

M=451 g TLC: R$_f$ (rac)=0.46 (PE/AcOEt 10:90) $^1$H-NMR (100 MHz, CDCl$_3$, TMS, δ), characteristics signals: Trans compound: 11.1 (1H, OH); 4.9 (t, 1H, H$_2$); 4.5 (m, 3H, H$_5$ and CH$_2$OH); 2.8–2.7 (m, 4H, CH$_2$NCH$_2$). Cis compound: 4.8–4.5 (m, 4H, H$_2$, H$_5$ and CH$_2$OH).

Step 3

2-(2'-fluorophenyl)-5-[N-[β-(3'-hydroxymethyl-4'-hydroxy-phenyl)-β-hydroxy-ethyl]-aminomethyl]-tetrahydrofuran I The compound I was obtained according to the process as described above (cf. example 1, step 3), starting from the compound V as obtained above in presence of PtO$_2$ instead of Pd/C (75%). M=361 g TLC: R$_f$(rac)=0.16 (CHCl$_3$/MeOH 80:20) HPLC: reverse phase column C$_{18}$-5μ, Nucleosil 125, CFCC 3F 10386; 150×4.6 mm: T$_R$min (rac)=16.5 (eluent MeOH/H$_2$O/TFA 25:75:0.5%—Flow rate 1 ml/min) IR (cm$^{-1}$), general absorption bands: $\nu_{OH}$ and $\nu_{NH}$=3400–3300; $\nu_O$=1,590; $\nu_{C\ OH}$=1220; $\nu_{C-O-C}$=1040; $\nu_{C-F}$=1230 $^1$H-NMR: δ (ppm) (cf table 1)

The fumarate salt was prepared by using the compound I as obtained above and fumaric acid. Melting point (°C.): mp (rac)=170

Example 7

2-(3'-methoxy-4'-propyloxy-5'-methylsulfonyl-phenyl)-5-[N-[β-(3'-hydroxymethyl-4'-hydroxy-phenyl)-β-hydroxy-phenyl)-β-hydroxy-ethyl]-aminomethyl]-tetrahydrofuran Compound I, with a 2,5-disubstitution in which n=1 and R=3-methoxy-4-propyloxy-5-methylsulfonyl phenyl.

Step 1

2-(3'-methoxy-4'-propyloxy-5'-methylsulfonyl-phenyl)-5-[N-benzyl-N-(3'-methoxycarbonyl-4'-hydroxy-phenacyl)]-aminomethyl-tetrahydrofuran IV The compound IV was obtained according to the process as described above (cf. example 1, step 1), starting from the appropriate starting compound II (74%).

M=625 g TLC: $R_f$(rac)=0.33 ($CH_2Cl_2$) IR (cm$^{-1}$): $\nu_{OH}$=3100; $\nu_{CO_2Me}$=1690; $\nu_{CO}$=1670 $^1$H-NMR (100 MHz, CDCl$_3$, TMS, $\delta$), characteristics signals: Trans compound: 11.2 (1H, OH); 8.5 (d, 1H, H$_2$'); 8.1 (2d, 1H, H$_6$); 7.3 (m, 5H, O); 6.9 (d, 1H, H$_5$'); 4.8 (t, 1H, H$_2$); 4.4 (m, 1H, H$_5$); 3.85 (m, 7H, CO$_2$Me, NCH$_2$CO, NCH$_2$O); 2.8 (d, 2H, CH$_2$N). Cis compound: 4.2 (m, 1H, H$_5$); 2.9 (d, 2H, CH$_2$N).

Step 2

2-(3'-methoxy-4'-propyloxy-5'-methylsulfonyl-phenyl)-5-[[N-benzyl-N-[$\beta$-hydroxy-$\beta$-(3'-hydroxymethyl-4'-hydroxy-phenyl)-ethyl]-aminomethyl]-tetrahydrofuran V The compound V was obtained according to the process as described above (cf. example 1, step 2), starting from the compound IV as obtained above (76%).

M=599 g TLC: $R_f$(rac)=0.37 ($CH_2Cl_2$/MeOH 95:5) $^1$H-NMR (100 MHz, CDCl$_3$, TMS, $\delta$), characteristics signals: Trans compound: 11.1 (1H, OH); 4.9 (t, 1H, H$_2$); 4.5 (m, 3H, H$_5$ and CH$_2$OH); 2.8–2.7 (m, 4H, CH$_2$NCH$_2$). Cis compound: 4.8–4.5 (m, 4H, H$_2$, H$_5$ and CH$_2$OH).

Step 3

2-(3'-methoxy-4'-propyloxy-5'-methylsulfonylphenyl)-5-[N-[$\beta$-(3'-hydroxymethyl-4'-hydroxy-phenyl)-$\beta$-hydroxy-ethyl]-aminomethyl]-tetrahydrofuran I The compound I was obtained according to the process as described above (cf. example 1, step 3), starting from the compound V as obtained above (75%). The cis and trans isomers are separated by preparative HPLC. M=509 g TLC: $R_f$(cis)=0.23 $R_f$(trans)=0.19 (CHCl$_3$/MeOH 80:20) HPLC: reverse phase column $C_{18}$-5$\mu$, Nucleosil 125, CFCC 3F 10386; 150×4.6 mm: $T_R$min (cis)=23; $T_R$min (trans)=19 (eluent H$_2$O/MeOH/TFA 60:40:0.5%—Flow rate 0.6 ml/min) IR (cm$^{-1}$), general absorption bands: $\nu_{OH}$ and $\nu_{NH}$=3400–3300; $\nu_O$=1590; $\nu_{C\;OH}$=1220; $\nu_{C-O-C}$=1040; $\nu_{SO_2Me}$=1305; $\nu_{OCH_3}$=1140 $^1$H-NMR: $\delta$ (ppm) (cf table 1)

The fumarate salt was prepared by using the compound I as obtained above and fumaric acid. Melting point (°C.): mp (cis) =156 mp (trans)=126

Example 8

2-(3',4'-dimethoxyphenyl)-5-[N-[$\beta$-(3'-hydroxymethyl-4'-hydroxy-phenyl)-$\beta$-hydroxyethyl]-aminomethyl]-tetrahydrofuran Compound I, with a 2.5-disubstitution in which n=1 and R=3,4-dimethoxyphenyl.

The steps 1 to 3 were performed as described above (cf. example 1, steps 1 to 3) to obtain the required compound. M=403 g TLC: $R_f$(cis)=0.27; $R_f$(trans)=0.22 (CHCl$_3$/MeOH 80:20) HPLC: reverse phase column $C_{18}$-5$\mu$, Nucleosil 125, CFCC 3F 10386; 150×4.6 mm: $T_R$min (cis)=13.6; $T_R$min (trans)=6.5 (eluent MeOH/H$_2$O/TFA 50:50:0.5%—Flow rate 0.5 ml/min) $^1$H-NMR: $\delta$ (ppm) (cf table 1)

The fumarate salt was prepared by using the compound I as obtained above and fumaric acid. Melting point(°C.): mp(cis)=118 mp (trans)=129

Example 9

2-(4'-methoxyphenyl)-5-[N-[$\beta$-(3'-hydroxymethyl-4'-hydroxy-phenyl)-$\beta$-hydroxy-ethyl]-aminomethyl]-tetrahydrofuran Compound I, with a 2,5-disubstitution in which n=1 and R=4-methoxyphenyl.

The steps 1 to 3 were performed as described above (cf. example 1, steps 1 to 3) to obtain the required compound. M=373 g TLC: $R_f$(cis)=0.22; $R_f$(trans)=0.19 (CHCl$_3$/MeOH 80:20) HPLC: reverse phase column $C_{18}$-5$\mu$, Nucleosil 125, CFCC 3F 10386; 150×4.6 mm: $T_R$min (cis)=45; $T_R$min (trans)=41 (eluent MeOH/H$_2$O/TFA 25:75:0.5%—Flow rate 1 ml/min) $^1$H-NMR: $\delta$ (ppm) (cf table 1)

The fumarate salt was prepared by using the compound I as obtained above and fumaric acid. Melting point (°C.): mp (cis)=101 mp (trans)=112

Example 10

2-(2',6'-dichlorophenyl)-5-[N-[$\beta$-(3'-hydroxymethyl-4'-hydroxy-phenyl)-$\beta$-hydroxy-ethyl]-aminomethyl]-tetrahydrofuran Compound I, with a 2,5-disubstitution in which n=1 and R=2,6-dichlorophenyl.

The steps 1 to 3 were performed as described above (cf. example 4, steps 1 to 3) to obtain the required compound. M=412 g TLC: $R_f$ (rac)=0.19 (CHCl$_3$/MeOH 80:20) HPLC: reverse phase column $C_{18}$-5$\mu$, Nucleosil 125, CFCC 3F 10386; 150×4.6 mm: $T_R$min=39 (eluent MeOH/H$_2$O/TFA 25:75:0.5%—Flow rate 1 ml/min) $^1$H-NMR: $\delta$ (ppm) (cf table 1)

The fumarate salt was prepared by using the compound I as obtained above and fumaric acid. Melting point (°C.): mp (rac)=92

Example 11

2-propyl-5-[N-[$\beta$-(3'-hydroxymethyl-4'-hydroxy-phenyl)-$\beta$-hydroxy-ethyl]-aminomethyl]-tetrahydrofuran Compound I, with a 2,5-disubstitution in which n=1 and R=propyl.

The steps 1 to 3 were performed as described above (cf. example 1, steps 1 to 3) to obtain the required compound. M=309 g TLC: $R_f$ (rac)=0.12 (CHCl$_3$/MeOH 80:20) HPLC: reverse phase column $C_{18}$-5$\mu$, Nucleosil 125, CFCC 3F 10386; 150×4.6 mm: $T_R$min=8.3 (eluent MeOH/H$_2$O/TFA 25:75:0.5%—Flow rate 1 ml/min) $^1$H-NMR: $\delta$ (ppm) (cf table 1)

The fumarate salt was prepared by using the compound I as obtained above and fumaric acid. Melting point (°C.): mp (rac)=127

Example 12

2-(4$\alpha$-pyridyl)-5-[N-[$\beta$-(3'-hydroxymethyl-4'-hydroxy-phenyl)-$\beta$-hydroxy-ethyl]-aminomethyl]-tetrahydrofuran Compound I, with a 2,5-disubstitution in which n=1 and R=4'-pyridyl.

Step 1

2-(4'-pyridyl)-5-[N-benzyl-N-(3'-methoxycarbonyl-4'-hydroxy-phenacyl)]-aminomethyl-tetrahydrofuran IV The compound IV was obtained according to the process as described above (cf. example 1, step 1), starting from the corresponding starting compound II (69%).

M=474 g. TLC: $R_f$ (rac)=0.25 (CHCl$_3$/MeOH 90:10).

Step 2

2-(4'-pyridyl)-5-[[N-benzyl-N-[β-hydroxy-β-(3'-hydroxymethyl-4'-hydroxy-phenyl)ethyl]-aminomethyl]-tetrahydrofuran V The compound V was obtained according to the process as described above (cf. example 1, step 2), starting from the corresponding compound IV (78%).

M=448 g TLC: $R_f$(rac)=0.20 (CHCl$_3$/MeOH 80:20)

Step 3

2-(4'-pyridyl)-5-[N-[β-(3'-hydroxymethyl-4'-hydroxyphenyl)-β-hydroxy-ethyl]-aminomethyl]-tetrahydrofuran I The compound I was obtained according to the process as described above (cf. example 1, step 3), starting from the corresponding compound V in presence of PtO$_2$ instead of Pd/C (72%). M=344 g TLC: $R_f$ (rac)=0.18 (CHCl$_3$/MeOH 60:40) HPLC: reverse phase column C$_{18}$-5μ, Nucleosil 125, CFCC 3F 10386; 150×4.6 mm: $T_R$min (rac)=12 (eluent MeOH/H$_2$O/TFA 15:85:0.5%—Flow rate 0.6 ml/min) IR (cm$^{-1}$), general absorption bands: $\nu_{OH}$ and $\nu_{NH}$=3400-3300; $\nu_O$=1590; $\nu_{C-OH}$=1220; $\nu_{C-O-C}$=1040; $\nu_{pyridine}$=1600 and 1560 $^1$H-NMR: δ (ppm) (cf table 1)

Example 13

2-phenyl-5-[N-[β-(3'-hydroxymethyl-4'-hydroxyphenyl)-β-hydroxy-ethyl]-aminoethyl]-tetrahydrofuran Compound I, with a 2,5-disubstitution in which n=2 and R=phenyl

Step 1

2-phenyl-5-[[N-benzyl-N-(3'-methoxycarbonyl-4'-hydroxy-phenacyl)]-aminoethyl-tetrahydrofuran IV The compound IV was obtained according to the process as described above (cf. example 1, step 1), starting from the appropriate compound II (73%).

TLC: $R_f$ (cis)=0.47 $R_f$ (trans)=0.43 (PE/AcOEt 60:40) IR (cm$^{-1}$): $\nu_{CO2Me}$=1690; $\nu_{CO}$=1675 $^1$H NMR (100 MHz, CDCl$_3$, TMS, δ) principal signals: Trans compound: 11.2 (1H, OH); 8.5 (d, 1H, H$_{2'}$); 8.1 (2d, 1H, H$_{6'}$); 7.3 (s, 5H, OCH$_2$); 4.9 (t, 1H, H$_2$); 4.2 (m, 1H, H$_5$); 4.1 (s, 5H, NCH$_2$CO and CO$_2$Me); 3.8 (2H, NCH$_2$O); 2.7 (t, 2H, CH$_2$N); 2.4–1.5 (m, 8H, H$_3$, H$_4$, 2CH$_2$ of the chain) Cis compound: 4.8 (t, 1H, H$_2$).

Step 2

2-phenyl-5-[[N-benzyl-N-[β-hydroxy-β-(3'-hydroxymethyl-4'-hydroxy-phenyl)ethyl]-aminoethyl]-tetrahydrofuran V The compound V was obtained according to the process as described above (cf. example 1, step 2), starting from the compound IV as obtained above (70%).

M=445 g TLC: $R_f$ (cis)=0.24 $R_f$ (trans)=0.28 (CHCl$_3$/MeOH 95:5) IR (cm$^{-1}$): $\nu_{OH}$=3400 $^1$H NMR (100 MHz, CDCl$_3$, TMS, δ) principal signals: Trans compound: 4.9 (t, 1H, H$_2$); 4.7 (s, 2H, CH$_2$OH); 4.6 (m, 1H, H$_5$); 4.15 (m, 1H, CHOH); 3.9 and 3.5 (2d, 2H, NCH$_2$O) Cis compound: 4.7 (m, 4H, H$_5$, H$_2$ and CH$_2$OH).

Step 3

2-phenyl-5-[N-[β-(3'-hydroxymethyl-4'-hydroxyphenyl)-β-hydroxy-ethyl]-aminoethyl]-tetrahydrofuran I The compound I was obtained according to the process as described above (cf. example 1, step 3), starting from the compound V as obtained above (71%). M=355 g TLC: $R_f$(cis)=0.48 $R_f$(trans)=0.40 (CHCl$_3$/MeOH 80:20) HPLC: reverse phase column C$_{18}$-5μ, Nucleosil 125, CFCC 3F 10386, 150×4.6 mm: $T_R$min(cis)=52; $T_R$min(trans)=48 (eluent: MeOH/H$_2$O/TFA 25:75:0.5%—Flow rate 1 ml/min) $^1$H-NMR: δ (ppm) (cf. table 2)

The fumarate salt was prepared by using the compound I as obtained above and fumaric acid. Melting point (°C.): mp (cis)=145 mp (trans)=130

Example 14

2-(3',4',5'-trimethoxyphenyl)-5-[N-[β-(3'-hydroxymethyl-4'-hydroxy-phenyl)[-β-hydroxy-ethyl]-aminoethyl]-tetrahydrofuran Compound I, with a 2,5-disubstitution in which n=2 and R=3,4,5-trimethoxyphenyl

Step 1

2-(3',4',5'-trimethoxyphenyl)-5-[[N-benzyl-N-(3'-methoxycarbonyl-4'-hydroxy-phenacyl)]-aminoethyl-tetrahydrofuran IV The compound IV was obtained according to the process as described above (cf. example 1, step 1), starting from the appropriate compound II.

TLC: $R_f$ (cis)=0.40 $R_f$ (trans)=0.28 (PE/AcOEt 50:50) IR (cm$^{-1}$): $\nu_{CO2Me}$=1690; $\nu_{CO}$=1675 $^1$H NMR (100 MHz, CDCl$_3$, TMS, δ) principal signals: Trans compound: 11.2 (1H, OH); 8.5 (d, 1H, H$_{2'}$); 8.1 (2d, 1H, H$_{6'}$); 7.3 (s, 5H, OCH$_2$); 4.9 (t, 1H, H$_2$); 4.2 (m, 1H, H$_5$); 4.1 (s, 5H, NCH$_2$CO and CO$_2$Me); 3.8 (2H, NCH$_2$O); 2.7 (t, 2H, CH$_2$N); 2.4–1.5 (m, 8H, H$_3$, H$_4$, 2CH$_2$ of the chain) Cis compound: 4.8 (t, 1H, H$_2$).

Step 2

2-(3',4',5'-trimethoxyphenyl)-5-[[N-benzyl-N-[β-hydroxy-β-(3'-hydroxymethyl-4'-hydroxy-phenyl)ethyl]-aminoethyl]-tetrahydrofuran V The compound V was obtained according to the process as described above (cf. example 1, step 2), starting from the compound IV as obtained above (72%).

M=535 g TLC: $R_f$ (cis)=0.60 $R_f$ (trans)=0.65 (CHCl$_3$/MeOH 80:20) IR (cm$^{-1}$): $\nu_{OH}$=3400 $^1$H NMR (100 MHz, CDCl$_3$, TMS, δ) principal signals: Trans compound: 4.9 (t, 1H, H$_2$); 4.7 (s, 2H, CH$_2$OH); 4.6 (m, 1H, H$_5$); 4.15 (m, 1H, CHOH); 3.9 and 3.5 (2d, 2H, NCH$_2$O) Cis compound: 4.7 (m, 4H, H$_5$, H$_2$ and CH$_2$OH)

Step 3

2-(3',4',5'-trimethoxyphenyl)-5-[N-[β-(3'-hydroxymethyl-4'-hydroxy-phenyl)-β-hydroxy-ethyl]-aminoethyl]-tetrahydrofuran I The compound I was obtained according to the process as described above (cf. example 1, step 3), starting from the compound V as obtained above (74%). M=455 g TLC: $R_f$(cis)=0.18 $R_f$(trans)=0.13 (CHCl$_3$/MeOH 80:20) HPLC: reverse phase column C$_{18}$-5μ, Nucleosil 125, CFCC 3F 10386, 150×4.6 mm: T$_R$min(cis)=24; T$_R$min(trans)=19.5 (eluent: MeOH/H$_2$O/TFA 25:75:0.5%—Flow rate 1 ml/min) $^1$H-NMR: δ (ppm) (cf. table 2)

The fumarate salt was prepared by using the compound I as obtained above and fumaric acid. Melting point (°C.): mp (cis)=180 mp (trans)=220

Example 15

2-(3',4',5'-trimethoxyphenyl)-5-[-N-[β-(3'-hydroxymethyl-4'-hydroxy-phenyl)-β-hydroxy-ethyl]-aminopropyl]-tetrahydrofuran Compound I, with a 2,5-disubstitution in which n=3 and R=3,4,5-trimethoxyphenyl

Step 1

2-(3',4',5'-trimethoxyphenyl)-5-[N-benzyl-N-(3'-methoxycarbonyl-4'-hydroxy-phenacyl)-aminopropyl]-tetrahydrofuran IV The compound IV was prepared according to the process as described above (cf. example 1, step 1), starting from the appropriate compound II (75%). TLC: $R_f$ (cis)=0.38 $R_f$ (trans)=0.26 (PE/AcOEt 50:50) IR (cm$^{-1}$): $\nu_{CO2Me}$=1690; $\nu_{CO}$=1675 $^1$H NMR (100 MHz, CDCl$_3$, TMS, δ) principal signals: Trans compound: 11.2 (1H, OH); 8.5 (d, 1H, H$_{2'}$); 8.1 (2d, 1H, H$_{6'}$); 7.3 (s, 5H, OCH$_2$); 4.9 (t, 1H, H$_2$); 4.2 (m, 1H, H$_5$); 4.1 (s, 5H, NCH$_2$CO and CO$_2$Me); 3.8 (2H, NCH$_2$O); 2.7 (t, 2H, CH$_2$N); 2.4–1.5 (m, 8H, H$_3$, H$_4$, 2CH$_2$ of the chain) Cis compound: 4.8 (t, 1H, H$_2$).

Step 2

2-(3',4',5'-trimethoxyphenyl)-5-[[N-benzyl-N-[β-hydroxy-β-(3'-hydroxymethyl-4'-hydroxy-phenyl)ethyl]-aminopropyl]-tetrahydrofuran V The compound V was prepared according to the process as described above (cf. example 1, step 2), starting from the compound IV as obtained above (78%).

M=547 g TLC: $R_f$ (cis)=0.36 $R_f$ (trans)=0.38 (CHCl$_3$/MeOH 90:10) IR (cm$^{-1}$): $\nu_{OH}$=3400 $^1$H NMR (100 MHz, CDCl$_3$, TMS, δ) principal signals: Trans compound: 4.9 (t, 1H, H$_2$); 4.7 (s, 2H, CH$_2$OH); 4.6 (m, 1H, H$_5$); 4.15 (m, 1H, CHOH); 3.9 and 3.5 (2d, 2H, NCH$_2$O) Cis compound: 4.7 (m, 4H, H$_5$, H$_2$ and CH$_2$OH).

Step 3

2-(3',4',5'-trimethoxyphenyl)-5-[-N-[β-(3'-hydroxymethyl-4'-hydroxy-phenyl)-β-hydroxy-ethyl]-aminopropyl]-tetrahydrofuran I The compound I was prepared according to the process as described above (cf. example 1, step 3), starting from the compound V as obtained above (72%).

M=457 g TLC: $R_f$ (cis)=0.18 $R_f$ (trans)=0.15 (CHCl$_3$/MeOH 80:20) HPLC: reverse phase column C$_{18}$-5μ, Nucleosil 125, CFCC 3F 10386, 150×4.6 mm: T$_R$min(cis)=38; T$_R$min(trans)=30 (eluent: MeOH/H$_2$O/TFA 25:75:0.5%—Flow rate 1 ml/min) $^1$H-NMR: δ (ppm) (cf. table 3)

The fumarate salt was prepared by using the compound I as obtained above and fumaric acid. Melting point (°C.): mp (cis)=205 mp (trans)=162

Example 16

2-(2'-chlorophenyl)-5-[N-[β-(3'-hydroxymethyl-4'-hydroxy-phenyl)-β-hydroxy-ethyl]-aminopropyl]-tetrahydrofuran Compound I, with a 2,5-disubstitution in which n=3 and R=2-chlorophenyl

Step 1

2-(2'-chlorophenyl)-5-[N-benzyl-N-(3'-methoxycarbonyl-4'-hydroxy-phenacyl)aminopropyl]-tetrahydrofuran IV The compound IV was prepared according to the process as described above (cf. example 1, step 1), starting from the appropriate compound II (75%).

TLC: $R_f$(rac)=0.40 (PE/AcOEt 70:30) IR (cm$^{-1}$): $\nu_{CO2Me}$=1690; $\nu_{CO}$=1675 $^1$H NMR (100 MHz, CDCl$_3$, TMS, δ) principal signals: Trans compound: 11.2 (1H, OH); 8.5 (d, 1H, H$_{2'}$); 8.1 (2d, 1H, H$_{6'}$); 7.3 (s, 5H, OCH$_2$); 4.9 (t, 1H, H$_2$); 4.2 (m, 1H, H$_5$); 4.1 (s, 5H, NCH$_2$CO and CO$_2$Me); 3.8 (2H, NCH$_2_O$); 2.7 (t, 2H, CH$_2$N); 2.4–1.5 (m, 8H, H$_3$, H$_4$, 2CH$_2$ of the chain) Cis compound: 4.8 (t, 1H, H$_2$).

Step 2

2-(2'-chlorophenyl)-5-[[N-benzyl-N-[β-hydroxy-β-(3'-hydroxymethyl-4'-hydroxyphenyl)ethyl]-aminopropyl]-tetrahydrofuran V The compound V was prepared according to the process as described above (cf. example 1, step 2), starting from the compound IV as obtained above (79%).

M=491.5 g TLC: $R_f$ (rac)=0.42 (CHCl$_3$/MeOH 95:5) IR (cm$^{-1}$): $\nu_{OH}$=3400 $^1$H NMR (100 MHz, CDCl$_3$, TMS, δ) principal signals: Trans compound: 4.9 (t, 1H, H$_2$); 4.7 (s, 2H, CH$_2$OH); 4.6 (m, 1H, H$_5$); 4.15 (m, 1H, CHOH); 3.9 and 3.5 (2d, 2H, NCH$_2$O) Cis compound: 4.7 (m, 4H, H$_5$, H$_2$ and CH$_2$OH).

Step 3

2-(2'-chlorophenyl)-5-[N-[β-(3'-hydroxymethyl-4'-hydroxy-phenyl)-β-hydroxy-ethyl]-aminopropyl]-tetrahydrofuran I The compound I was prepared according to the process as described above (cf. example 1, step 3), starting from the compound V as obtained above, in presence of PtO$_2$ instead of Pd/C (73%). M=401.5 g TLC: $R_f$(rac)=0.14 (CHCl$_3$/MeOH 80:20) HPLC: reverse phase column C$_{18}$-5μ, Nucleosil 125, CFCC 3F 10386, 150×4.6 mm: T$_R$min(rac)=19.4 (eluent: MeOH/H$_2$O/TFA 25:75:0.5%—Flow rate 1 ml/min) $^1$H-NMR: δ (ppm) (cf. table 3)

The fumarate salt was prepared by using the compound I as obtained above and fumaric acid. Melting point (°C.): mp (rac)=210

Example 17

2-(3',4',5'-trimethoxyphenyl)-5-[N-[β-(3'-hydroxymethyl-4'-hydroxy-phenyl)-β-hydroxy-ethyl]-aminoheptyl-tetrahydrofuran Compound I, with a 2,5-disubstitution in which n=7 and R=3,4,5-trimethoxyphenyl.

The steps 1 to 3 were performed as described above (cf. example 1, steps 1 to 3) to obtain the required compound. M=513 g TLC: $R_f$(trans)=0.19 (CHCl$_3$/MeOH 80:20) HPLC: reverse phase column C$_{18}$-5μ, Nucleosil 125, CFCC 3F 10386, 150×4.6 mm: T$_R$min(trans)=35 (eluent MeOH/H2O/TFA 25:75:0.5%—Flow rate 1 ml/min) $^1$H-NMR: δ (ppm) (cf. table 4)

The fumarate salt was prepared by using the compound I as obtained above and fumaric acid. Melting point (°C.): mp (trans)=156

Example 18

2-(3',4',5'-trimethoxyphenyl)-4-[N-β-(3'-hydroxymethyl-4'-hydroxy-phenyl)-β-hydroxy-ethyl]-aminomethyl]-tetrahydrofuran Compound I, with a 2,4-disubstitution in which n=1 and R=3,4,5-trimethoxyphenyl

Step 1

2-(3',4',5'-trimethoxyphenyl)4[N-benzyl-N-(3'-methoxycarbonyl-4'-hydroxy-phenacyl)-aminomethyl]-tetrahydrofuran IV The compound IV was prepared according to the process as described above (cf. example 1, step 1), starting from the appropriate amine II (yield 69%).

TLC: R$_f$(rac)=0.42 (PE/AcOEt 50:50) IR (cm$^{-1}$): ν$_{CO}$ (ester and ketone)=1690 $^1$H NMR (100 MHz, CDCl$_3$, TMS, δ) characteristics signals: 4.7 (m, 1H, H$_2$); 4.2–3.5 (m, 16H, 4CH$_3$O, NCH$_2$CO, NCH$_2$O); 2.7–1.7 (m, 5H, 2H$_3$, 1H$_4$ and CH$_2$N).

Step 2

2-(3',4',5'-trimethoxyphenyl)-4-[-N-benzyl-N-[β-(3'-hydroxymethyl-4'-hydroxyphenyl)-β-hydroxy-ethyl]-aminomethyl]-tetrahydrofuran V The compound V was prepared according to the process as described above (cf. example 1, step 2), starting from the compound IV as obtained above (yield 70%).

TLC: R$_f$ (rac)=0.27 (CHCl$_3$/MeOH 85:15) IR (cm$^{-1}$): ν$_{OH}$=3450–3300 $^1$H NMR (100 MHz, CDCl$_3$, TMS, δ), characteristics signals: 11 (phenolic OH); 7.3–6.8 (m, 8H, O and H$_9$, H$_{10}$, H$_{11}$); 6.5 (d, 2H, O); 4.8 (m, 3H, OH, H$_2$ and H$_{12}$); 3.8 (m, 14H, 3CH$_3$O, 2H$_5$, NCH$_2$O and H$_8$); 2.6–1.9 (m, 8H, 3OH, H$_6$, H$_7$ and H$_4$).

Step 3

2-(3',4',5'-trimethoxyphenyl)-4-[N-β-(3'-hydroxymethyl-4'-hydroxy-phenyl)-β-hydroxy-ethyl]-aminomethyl]-tetrahydrofuran I After hydrogenolysis of the compound V, the compound I thus obtained was purified by chromatography on a silica column (eluent CHCl$_3$/MeOH 95:5, 90:10 then 70:30) (74%). M=433 g TLC: R$_f$ (rac)=0.23 (CHCl$_3$/MeOH 80:20) $^1$H-NMR: δ (ppm) (cf. table 5) HPLC: reverse phase column C$_{18}$-5μ, Nucleosil 125, CFCC 3F 10386, 150×4.6 mm: T$_R$min=7.5 (eluent MeOH/H$_2$O/TFA 25:75:0.5%—Flow rate 1 ml/min).

The fumarate salt was prepared by using the compound I as obtained above and fumaric acid. M=549 g; Melting point (°C.): 118

Example 19

2-(2'-chlorophenyl)-4-[N-[β-(3'-hydroxymethyl-4'-hydroxy-phenyl)-β-hydroxy-ethyl]-aminomethyl]-tetrahydrofuran Compound I, with a 2,4-disubstitution in which n=1 and R=2-chlorophenyl

Step 1

2-(2'-chlorophenyl)-4-[N-benzyl-N-(3'-methoxycarbonyl-4'-hydroxy-phenacyl)]-aminomethyl]-tetrahydrofuran IV The compound IV was prepared according to the process as described above (cf. example 1, step 1), starting from the appropriate compound II (yield 67%).

TLC: R$_f$(rac)=0.46 (PE/AcOEt 50:50) IR (cm$^{-1}$): ν$_{CO}$ (ester and ketone)=1690 $^1$H NMR (100 MHz, CDCl$_3$, TMS, δ)characteristics signals: 4.7 (m, 1H, H$_2$); 4.2–3.5 (m, 7H, CH$_3$O, NCH$_2$CO, NCH$_2$O); 2.7–1.7 (m, 5H, 2H$_3$, 1H$_4$ and CH$_2$N).

Step 2

2-(2'-chlorophenyl)-4-[-N-benzyl -N-[β-(3'-hydroxymethyl-4'-hydroxy-phenyl)-β-hydroxy-ethyl]-aminomethyl]-tetrahydrofuran V The compound V was prepared according to the process as described above (cf. example 1, step 2), starting from the compound IV as obtained above (yield 71%).

TLC: R$_f$ (rac)=0.29 (CHCl$_3$/MeOH 85:15) IR (cm$^{-1}$): ν$_{OH}$=3450–3300 $^1$H-NMR (100 MHz, CDCl$_3$, TMS, δ) characteristics signals: 11 (phenolic OH); 7.3–6.8 (m, 8H, O and H$_9$, H$_{10}$, H$_{11}$); 4.8 (m, 3H, OH, H$_2$ and H$_{12}$); 3.8 (m, 5H, 2H$_5$, NCH$_2$O and H$_8$); 2.6–1.9 (m, 8H, 3OH, H$_6$, H$_7$ and H$_4$).

Step 3

2-(2'-chlorophenyl)-4-[N-[β-(3'-hydroxymethyl-4'-hydroxy-phenyl)-β-hydroxy-ethyl]-aminomethyl]-tetrahydrofuran I The compound I was prepared according to the process as described above (cf. example 1, step 3), starting from the compound V as obtained above in presence of PtO$_2$ instead of Pd/C.

TLC: R$_f$(rac)=0.19 (CHCl$_3$/MeOH 80:20) HPLC: reverse phase column C$_{18}$-5μ, Nucleosil 125, CFCC 3F 10386, 150×4.6 mm: T$_R$min=38 (eluent MeOH/H$_2$O/TFA 25:75:0.5%—Flow rate 1 ml/min). $^1$H-NMR: δ (ppm) (cf. table 5)

The fumarate salt was prepared by using the compound I as obtained above and fumaric acid. M=493.5 g; Melting point (°C.): 79

Table 1

$^1$H-NMR (100 MHz, CD$_3$OD, TMS, δ): the exchangeable protons are not visible. δ (ppm) according to the following formula:

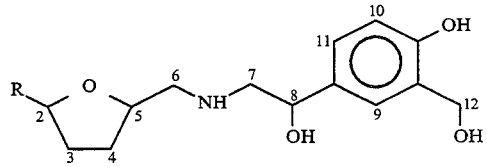

Example 1

Racemic: 7.3 (s, 5H); 7.1–6.6 (m, 3H, H$_9$, H$_{10}$, H$_{11}$); 4.9 (m, 1H, H$_2$); 4.6 (s, 2H, H$_{12}$); 4.4 (m, 2H, H$_5$ and H$_8$); 2.8 (m, 4H, H$_6$ and H$_7$); 2.3–1.7 (m, 4H, H$_3$ and H$_4$)

Example 2

Trans: 7.4–6.9 (m, 3H, H$_9$, H$_{10}$, H$_{11}$); 6.8 (s, 2H, O); 5.2 (m, 3H, H$_2$ and H$_{12}$); 4.7 (m, 2H, H$_5$ and H$_8$); 3.9 (d, 9H, 3CH$_3$O); 3.15 (m, 4H, H$_6$ and H$_7$); 2.5–1.9 (m, 4H, H$_3$ and H$_4$) Cis: 5 (m, 3H, H$_2$ and H$_{12}$); 4.5 (m, 1H, H$_5$)

Example 3

Trans: 7.2–6.9 (2m, 5H, H$_9$, H$_{10}$, H$_{11}$ and O); 5.3 (m, 1H, H$_2$); 5.1 (s, 2H, H$_{12}$); 4.9 (m, 1H, H$_5$); 4.7 (m, 1H, H$_8$); 3.9 (d, 9H, 3CH$_3$O); 3.15 (m, 4H, H$_6$ and H$_7$); 2.5–1.9 (m, 4H, H$_3$ and H$_4$) Cis: 4.5 (m, 1H, H$_5$)

Example 4

Trans: 7.6–7.3 (m, 6H, H$_9$, H$_{11}$ and O); 6.9 (d, 1H, H$_{10}$); 5.5 (t, 1H, H$_2$); 4.9 (m, 3H, H$_{12}$ and H$_8$); 4.7 (m, 1H, H$_5$); 3.2 (m, 4H, H$_6$ and H$_7$); 2.6–1.9 (m, 4H, H$_3$ and H$_4$) Cis: 5.4 (t, 1H, H$_2$); 4.5 (m, 1H, H$_5$); 3.3 (m, 4H, H$_6$ and H$_7$)

Example 5

Trans: 7.6–7.3 (m, 6H, H$_9$, H$_{11}$ and O); 6.9 (d, 1H, H$_{10}$); 5.3 (t, 1H, H$_2$); 4.8 (m, 4H, H$_{12}$, H$_8$ and H$_5$); 3.1 (m, 4H, H$_6$ and H$_7$); 2.6–1.7 (m, 4H, H$_3$ and H$_4$) Cis: 4.4 (m, 1H, H$_5$); 3.3 (m, 4H, H$_6$ and H$_7$)

Example 6

Racemic: 7.5–7 (m, 6H, H$_9$, H$_{11}$ and O); 6.9 (d, 1H, H$_{10}$); 5.4 (m, 1H, H$_2$); 4.7 (m, 3H, H$_8$ and H$_{12}$); 4.6 (m, 1H, H$_5$); 3.1 (m, 4H, H$_6$ and H$_7$); 2.6–1.7 (m, 4H, H$_3$ and H$_4$)

Example 7

Trans: 7.6–7 (m, 4H, H$_9$, H$_{11}$ and O); 6.9 (d, 1H, H$_{10}$); 4.9 (m, 1H, H$_2$); 4.7 (m, 3H, H$_{12}$ and H$_8$); 4.5 (m, 1H, H$_5$); 4 (t, 2H, OCH$_2$); 3.8 (s, 3H, OCH$_3$); 3.2 (1, 3H, SO$_2$CH$_3$); 3 (m, 4H, H$_6$ and H$_7$); 2.6–1.6 (m, 6H, CH$_2$, H$_3$ and H$_4$); 0.9 (t, 3H, CH$_3$) Cis: 4.7 (m, 1H, H$_2$); 4.3 (m, 1H, H$_5$); 3.2 (m, 7H, SO$_2$CH$_3$, H$_6$ and H$_7$)

Example 8

Trans: 7.4–7 (m, 3H, H$_9$, H$_{10}$, H$_{11}$); 6.8 (m, 3H, O); 5.2 (m, 3H, H$_2$ and H$_{12}$); 4.7 (m, 2H, H$_5$ and H$_8$); 3.8 (s, 6H, 2CH$_3$O); 3.2 (m, 4H, H$_6$ and H$_8$); 2.5–1.9 (m, 4H, H$_3$ and H$_4$) Cis: 5 (m, 3H, H$_2$ and H$_{12}$); 4.5 (m, 1H, H$_5$)

Example 9

Trans: 7.4–7 (m, 5H, H$_9$, H$_{10}$, H$_{11}$, O); 6.8 (d, 2H, H in α of OMe); 5.2 (m, 3H, H$_2$ and H$_{12}$); 4.7 (m, 2H, H$_5$ and H$_8$); 3.8 (s, 3H, OCH$_3$); 3.15 (m, 4H, H$_6$ and H$_7$); 2.15–1.9 (m, 4H, H$_3$ and H$_4$) Cis: 5 (m, 3H, H$_2$ and H$_{12}$); 4.5 (m, 1H, H$_5$)

Example 10

Racemic: 7.5–6.9 (m, 6H, H$_9$, H$_{10}$, H$_{11}$, O); 5.5 (t, 1H, H$_2$); 4.9 (m, 3H, H$_{12}$ and H$_8$); 4.6 (m, 1H, H$_5$); 3.2 (m, 4H, H$_6$ and H$_7$); 2.6–1.9 (m, 4H, H$_3$ and H$_4$)

Example 11

Racemic: 7–6.6 (m, 3H, H$_9$, H$_{10}$, H$_{11}$); 5 (s, 2H, H$_{12}$); 4.8 (m, 1H, H$_8$); 4.1–3.9 (m, 2H, H$_2$ and H$_5$); 3.2 (m, 4H, H$_6$ and H$_7$); 2.3–1.4 (m, 8H, 4CH$_2$); 0.9 (t, 3H, CH$_3$)

Example 12

Racemic: 8.5 (m, 2H, 2H$_α$N); 7.4–6.9 (m, 5H, 2H pyridine, H$_9$, H$_{10}$, H$_{11}$); 5 (m, 1H, H$_2$); 4.8–4.5 (m, 4H, H$_5$, H$_8$ and 2H$_{12}$); 3.1 (m, 4H, H$_6$ and H$_7$); 2.6–1.9 (m, 4H, H$_3$ and H$_4$)

Table 2

$^1$H-NMR (100 MHz, CD$_3$OD, TMS, δ), characteristics signals: δ (ppm) according to the following formula:

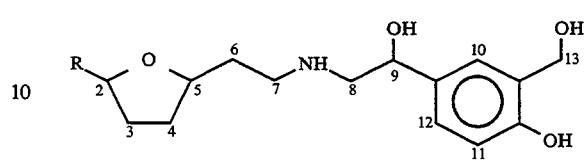

Example 13

Trans: 7.3 (s, 5H); 7.1–6.6 (m, 3H, H$_{10}$, H$_{11}$, H$_{12}$); 5.1 (s, 2H, H$_{13}$); 5 (m, 2H, H$_2$ and H$_9$); 4.1 (m, 1H, H$_5$); 3.2 (m, 2H, H$_8$); 2.75 (m, 2H, H$_7$); 2–1.4 (m, 6H, H$_3$, H$_4$ and H$_6$) Cis: 4.9 (m, 2H, H$_2$ and H$_9$); 3.9 (m, 1H, H$_5$)

Example 14

Trans: 7.4–6.9 (m, 3H, H$_{10}$, H$_{11}$, H$_{12}$); 6.8 (s, 2H, O); 5.2 (s, 2H, H$_{13}$); 5 (m, 1H, H$_2$); 4.8 (m, 1H, H$_9$); 4.6 (m, 1H, H$_5$); 3.9 (d, 9H, 3CH$_3$O); 3.2 (m, 2H, H$_5$); 2.5 (m, 2H, H$_7$); 2.2–1.7 (m, 6H, H$_3$, H$_4$, H$_6$) Cis: 4.8 (m, 1H, H$_8$); 4.3 (m, 1H, H$_5$)

Table 3

$^1$H-NMR (100 MHz, CD$_3$OD, TMS, δ), characteristics signals: δ (ppm) according to the following formula:

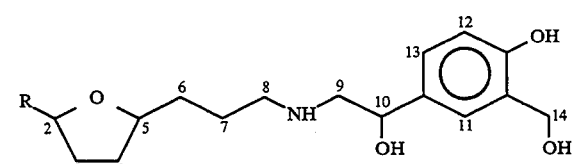

Example 15

Trans: 7.5–6.9 (m, 3H, H$_{11}$, H$_{12}$, H$_{13}$); 6.7 (s, 2H, O); 5.1 (m, 2H, H$_2$ and H$_{10}$); 4.9 (s, 2H, H$_{14}$); 4.3 (m, 1H, H$_5$); 3.9 (d, 9H, 3CH$_3$O); 3.2 (m, 4H, H$_8$ and H$_9$); 2.6–1.7 (m, 8H, H$_6$, H$_7$, H$_3$ and H$_4$) Cis: 5 (m, 4H, H$_2$, H$_{10}$ and H$_{14}$); 4.1 (m, 1H, H$_5$)

Example 16

Racemic: 7.7–6.8 (m, 7H, H$_{11}$, H$_{12}$, H$_{13}$ and O); 5.4 (m, 1H, H$_2$); 5.1 (s, 2H, H$_{14}$); 4.9 (m, 1H, H$_{10}$); 4.3 (m, 1H, H$_5$); 3.2 (m, 4H, H$_8$ and H$_9$); 2.2–1.3 (m, 8H, H$_6$, H$_7$, H$_3$ and H$_4$)

Table 4

$^1$H-NMR (100 MHz, CD$_3$OD, TMS, δ), characteristics signals: δ (ppm) according to the following formula:

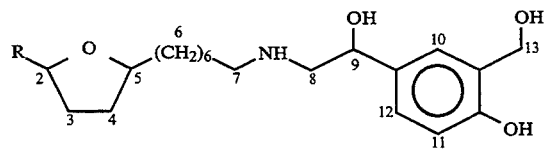

Example 17

Trans: 7.4–6.9 (m, 3H, $H_{10}$, $H_{11}$, $H_{12}$); 6.7 (s, 2H, O); 5.1 (m, 2H, $H_2$ and $H_9$); 4.3 (m, 1H, $H_5$); 3.9 (d, 9H, 3$CH_3O$); 3.2 (m, 4H, t17 and $H_5$); 2.6–1.7 (m, 16H, $H_3$, $H_4$ and 6$CH_2$)

Table 5

$^1H$ NMR (100 MHz, $CD_3OD$, TMS, δ) characteristics signals: δ (ppm) according to the following formula:

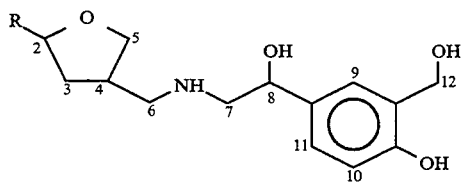

Example 18

7.5–6.8 (m, 3H, $H_9$, $H_{10}$, $H_{11}$); 6.7 (d, 2H, O); 4.8 (m, 3H, $H_2$ and $H_{12}$); 4.3 (m, 1H, $H_5$); 3.8 (m, 11H, 3$CH_3O$ and 2$H_5$); 2.8 (m, 4H, $H_6$ and $H_7$); 2.3 (m, 3H, $H_3$ and $H_4$)

Example 19

7.5–6.8 (m, 6H, $H_9$, $H_{11}$ and O); 6.9 (d, 1H, $H_{10}$); 5 (m, 3H, $H_2$ and $H_{12}$); 4.4 (m, 1H, $H_8$); 3.8 (m, 2H, 2$H_5$); 2.8 (m, 4H, $H_6$ and $H_7$); 2.3 (m, 3H, 2$H_3$ and $H_4$)

Toxicology

No toxicity was noticed for any of the compounds according to the invention when administered per se, at doses up to 50 mg/kg, to rats and mice. By the IP route, no death was noticed at 30 mg/kg for the same animals.

Pharmacology

Compounds of the invention are potent $\beta_2$ adrenoceptor agonists with a long duration of action on airways smooth muscles and act as bronchodilatators in vivo.

In vitro, radioligand binding studies in lung membrane indicated that several of them have a better affinity for β adrenoceptors than Salbutamol, used as a reference. The results are summarised in Table A. Generally, the activity is better for the trans than the cis isomer.

In vivo

The different compounds showed a bronchodilatator effect with a duration of action better than Salbutamol in its ability to inhibit acetylcholine induced bronchoconstriction.

Method

Male Hartley Guinea Pigs (450–500 g) were anaesthetised with ethyl carbamate and prepared for recording bronchoconstriction according to Konzett and Rossler method (Naunym Schmiedebergers Arch. Exp. Path. Pharmakol (1940) 195, 71). To abolish spontaneous respiration, an injection IV of vecuronium bromide (2 mg/kg) was made. Bronchoconstriction was induced by IV injection of Acetylcholine and the animals received one dose of β agonist compound (IV) 5 minutes later. Results are given with Salbutamol as reference and are summarised in Table B.

Moreover, the example 2 (cis) showed an α-antagonist activity (binding α, receptor Ki=61 nM) and was an inhibitor of isolated aorta contraction induced by phenylephrine (p$A_2$: 7.75).

Compounds of the invention compared to Salbutamol, are not more active but their actions lost a longer time which is a very important advantage.

Presentation-Posology

In human therapy, a daily dose is of from 0.01 to 50 mg; for oral administration, the pharmaceutical composition may take the form of, for instance, tablets or capsules; by this route, the suitable doses are 0.01 mg to 50 mg. By IP route, the corresponding daily doses are 0.01 mg to 20 mg.

TABLE A

|  | BINDING AFFINITY (Ki, nM) |
| --- | --- |
| Salbutamol | 2500 |
| Example 1 | 410 |
| Example 2 (trans) | 80 |
| Example 2 (cis) | 410 |
| Example 2 (trans) (+) | 50 |
| Example 2 (trans) (−) | 350 |
| Example 3 (trans) | 1600 |
| Example 4 (trans) | 400 |
| Example 4 (cis) | 347 |
| Example 5 (trans) | 750 |
| Example 5 (cis) | 760 |
| Example 6 | 1800 |
| Example 8 (trans) | 1050 |
| Example 8 (cis) | 1100 |
| Example 9 (trans) | 590 |
| Example 9 (cis) | 810 |
| Example 11 | 520 |
| Example 12 | 350 |
| Example 14 (cis) | 1900 |
| Example 15 (trans) | 760 |
| Example 15 (cis) | 1900 |
| Example 16 | 570 |
| Example 18 | 1600 |

TABLE B

| COMPOUNDS | DOSE μmol/kg, IV | DURATION OF ACTION (mn) | BRONCHOCONSTRICTION PROTECTION SCORE | | |
| --- | --- | --- | --- | --- | --- |
|  |  |  | 5 mn | 15 mn | 30 mn |
| Salbutamol | 0.13 | 10 | +++ | 0 | 0 |
|  | 0.42 | 30 | +++ | +++ | 0 |
| Example 1 | 4.8 | 0 | 0 | 0 | 0 |
| Example 2 (trans) | 0.13 | 30 | +++ | ++ | + |
|  | 0.42 | >50 | +++ | +++ | +++ |
| Example 2 (cis) | 4.6 | 5 | + | 0 | 0 |
| Example 3 (trans) | 1.53 | 5 | + | 0 | 0 |
|  | 3.6 | 30 | ++ | + | + |
| Example 4 (trans) | 0.46 | 10 | +++ | 0 | 0 |
|  | 1.48 | >25 | +++ | ++ | ++ |
| Example 4 (cis) | 0.46 | 10 | ++ | 0 | 0 |

TABLE B-continued

| COMPOUNDS | DOSE µmol/kg, IV | BRONCHOCONSTRICTION PROTECTION | | | |
|---|---|---|---|---|---|
| | | DURATION OF ACTION (mn) | SCORE | | |
| | | | 5 mn | 15 mn | 30 mn |
| | 1.5 | <40 | ++ | ++ | + |
| Example 5 (trans) | 0.46 | >20 | ++ | + | + |
| Example 5 (cis) | 0.47 | <10 | + | 0 | 0 |
| Example 6 | 0.47 | <30 | ++ | + | + |
| Example 8 (trans) | 0.13 | 30 | ++ | + | + |
| | 0.46 | >30 | ++ | ++ | + |
| Example 8 (cis) | 0.48 | <30 | ++ | + | 0 |
| Example 9 (trans) | 0.46 | >30 | +++ | ++ | + |
| Example 9 (cis) | 0.46 | 20 | ++ | + | 0 |
| Example 12 | 0.13 | >30 | ++ | + | + |
| | 0.42 | >30 | ++ | ++ | + |
| Example 14 (cis) | 1.50 | 30 | +++ | + | + |
| Example 15 (trans) | 0.42 | 20 | +++ | ++ | 0 |
| | 4.18 | >50 | +++ | +++ | ++ |
| Example 16 | 1.6 | >15 | + | + | 0 |
| Example 18 | 1.6 | 30 | ++ | + | + |

The score legends are as follows:
Score 0: inhibition <20%
Score +: inhibition = 20–50%
Score ++: inhibition = 50–75%
Score +++: inhibition >75%.

We claim:
1. An N-(2,5-disubstituted tetrahydrofuryl alkyl)-N-(phenylethyl-β-ol)amine derivative, of racemic or enantiomer form, of general formula I

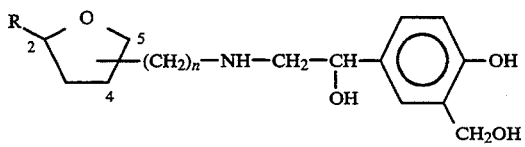

wherein
R represents a straight or branched alkyl group comprising from 1 to 10 carbon atoms; a heteroaryl group, a phenyl radical or a substituted phenyl radical of the formula

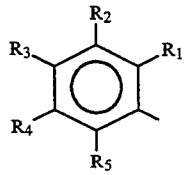

in which the radicals $R_1$, $R_2$, $R_3$, $R_4$ and $R_5$ independently represent a hydrogen atom, a halogen atom, an alkoxy radical comprising from 1 to 5 carbon atoms, or an alkylsulphonyl radical comprising from 1 to 5 carbon atoms;
n is from 1 to 10;
and pharmaceutically acceptable salts thereof.

2. Pharmaceutical composition comprising a derivative according to claim 1, or a pharmaceutically acceptable salt of such a derivative, in admixture with a pharmaceutically acceptable diluent or carrier.

3. An N-(2,4-disubstituted tetrahydrofuryl alkyl)-N-(phenylethyl-β-ol)amine derivative, of racemic or enantiomer form, of general formula I

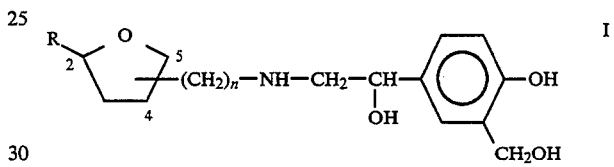

wherein
R represents a straight or branched alkyl group comprising from 1 to 10 carbon atoms; a heteroaryl group, a phenyl radical or a substituted phenyl radical of the formula

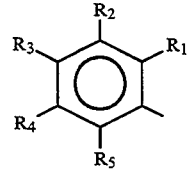

in which the radicals $R_1$, $R_2$, $R_3$, $R_4$ and $R_5$ independently represent a hydrogen atom, a halogen atom, an alkoxy radical comprising from 1 to 5 carbon atoms, or an alkylsulphonyl radical comprising from 1 to 5 carbon atoms;
n is 1;
and pharmaceutically acceptable salts thereof.

4. Pharmaceutical composition comprising a derivative according to claim 3, or a pharmaceutically acceptable salt of such a derivative, in admixture with a pharmaceutically acceptable diluent or carrier.

5. An N-(2,4-disubstituted tetrahydrofuryl alkyl)-N-(phenylethyl-β-ol)amine derivative, of racemic or enantiomer form, of general formula I

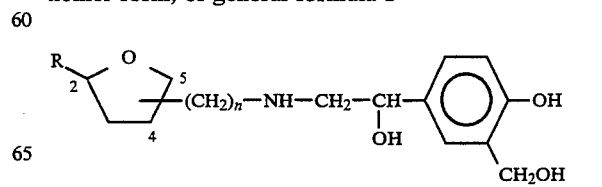

wherein

R represents a straight or branched alkyl group comprising from 1 to 10 carbon atoms; a phenyl radical or a substituted phenyl radical of the formula

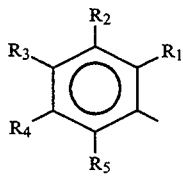

in which the radicals $R_1$, $R_2$, $R_3$, $R_4$ and $R_5$ independently represent a hydrogen atom, a halogen atom, an alkoxy radical comprising from 1 to 5 carbon atoms, or an alkylsulphonyl radical comprising from 1 to 5 carbon atoms;

n is 1 to 10;

and pharmaceutically acceptable salts thereof.

6. Pharmaceutical composition comprising a derivative according to claim 5 or a pharmaceutically acceptable salt of such a derivative, in admixture with a pharmaceutically acceptable diluent or carrier.

* * * * *